United States Patent
Van Sciver

(10) Patent No.: US 9,440,317 B2
(45) Date of Patent: Sep. 13, 2016

(54) POST-CRIMPING INSPECTION OF SCAFFOLDS MOUNTED ON SCAFFOLD DELIVERY SYSTEMS

(71) Applicant: Abbott Cardiovascular Systems Inc., Santa Clara, CA (US)

(72) Inventor: Jason Van Sciver, Los Gatos, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 478 days.

(21) Appl. No.: 13/735,871

(22) Filed: Jan. 7, 2013

(65) Prior Publication Data
US 2014/0189994 A1 Jul. 10, 2014

(51) Int. Cl.
B23P 11/00 (2006.01)
A61F 2/958 (2013.01)
A61F 2/95 (2013.01)

(52) U.S. Cl.
CPC .............. B23P 11/005 (2013.01); A61F 2/958 (2013.01); *A61F 2002/9522* (2013.01); *A61F 2002/9583* (2013.01); *Y10T 29/49769* (2015.01); *Y10T 29/53022* (2015.01)

(58) Field of Classification Search
CPC ........... A61F 2/958; A61F 2002/9583; A61F 2002/9522; A61F 2002/9528; B23P 11/005; Y10T 29/49769; Y10T 29/53022; A61M 25/104; A61M 25/1027
See application file for complete search history.

(56) References Cited

U.S. PATENT DOCUMENTS

| | | | |
|---|---|---|---|
| 6,464,723 B1 * | 10/2002 | Callol | 623/1.34 |
| 6,606,403 B2 * | 8/2003 | Freifeld | 382/152 |
| 6,629,350 B2 | 10/2003 | Motsenbocker | |
| 6,931,899 B2 | 8/2005 | Goff et al. | |
| 7,010,850 B2 | 3/2006 | Hijlkema et al. | |
| 7,316,148 B2 | 1/2008 | Asmus et al. | |
| 7,761,968 B2 | 7/2010 | Huang et al. | |
| 7,762,804 B1 | 7/2010 | Stupecky | |
| 7,886,419 B2 | 2/2011 | Huang et al. | |
| 7,945,409 B2 | 5/2011 | Furst et al. | |
| 8,002,817 B2 | 8/2011 | Limon | |
| 8,123,793 B2 | 2/2012 | Roach et al. | |
| 8,225,474 B2 * | 7/2012 | Arcand et al. | 29/272 |
| 8,261,423 B2 * | 9/2012 | Jow | B29C 65/72 29/447 |
| 8,311,312 B1 * | 11/2012 | Richardson | 382/141 |
| 8,388,673 B2 | 3/2013 | Yang et al. | |

(Continued)

FOREIGN PATENT DOCUMENTS

WO WO 2012/177777 12/2012

OTHER PUBLICATIONS

Bosiers et al., "Coronary and endovascular applications of the Absorb™ bioresorbable vascular scaffold", Interv. Cardiol. 4(6), pp. 621-631 (2012).

(Continued)

*Primary Examiner* — Alexander P Taousakis
(74) *Attorney, Agent, or Firm* — Squire Patton Boggs (US) LLP

(57) ABSTRACT

A system for mounting a scaffold on a balloon catheter includes two positioning and alignment stations, which are used to prepare a scaffold and catheter for crimping using the same crimping head. The system is configured for automated assembly of the scaffold and catheter prior to crimping and performing post-crimping inspection for the crimped scaffold and prior to placing a restraining sheath over the crimped scaffold.

20 Claims, 10 Drawing Sheets

(56) References Cited

U.S. PATENT DOCUMENTS

| | | | |
|---|---|---|---|
| 9,072,590 B2* | 7/2015 | Wang ................ A61F 2/0095 |
| 2003/0070469 A1 | 4/2003 | Kokish | |
| 2004/0044279 A1* | 3/2004 | Lewin ................ G01R 33/4833 600/407 |
| 2005/0143752 A1 | 6/2005 | Schwager et al. | |
| 2005/0159802 A1* | 7/2005 | Furst et al. .................. 623/1.11 |
| 2007/0006441 A1* | 1/2007 | McNiven et al. .............. 29/508 |
| 2007/0289117 A1 | 12/2007 | Huang et al. | |
| 2009/0088829 A1* | 4/2009 | Wang ................ A61F 2/958 623/1.11 |
| 2009/0299452 A1* | 12/2009 | Eidenschink et al. ....... 623/1.11 |
| 2010/0014747 A1* | 1/2010 | Freifeld ................ 382/141 |
| 2011/0059227 A1* | 3/2011 | Pacetti et al. ................ 427/2.25 |
| 2011/0270383 A1* | 11/2011 | Jow et al. .................... 623/1.16 |
| 2011/0271513 A1 | 11/2011 | Wang | |
| 2011/0307046 A1 | 12/2011 | Bourang et al. | |
| 2012/0010693 A1* | 1/2012 | Van Sciver ................ 623/1.11 |
| 2012/0042501 A1 | 2/2012 | Wang et al. | |
| 2012/0285609 A1* | 11/2012 | Wang ................ A61L 31/06 156/156 |
| 2014/0096357 A1* | 4/2014 | Wang ................ A61F 2/958 29/446 |
| 2014/0335143 A1* | 11/2014 | Lim et al. ................... 424/423 |
| 2015/0018934 A1* | 1/2015 | Pacetti ........................ 623/1.16 |

OTHER PUBLICATIONS

Miller "Abbott's Bioresorbable Stent Shows Durable Results in ABSORB Trial", The Gray Sheet, pp. 17-18, Mar. 2003.
U.S. Appl. No. 13/708,638, filed Dec. 7, 2012, Wang et al.
International Search Report and Written Opinion for PCT/US2013/075431, mailed Oct. 27, 2014, 16 pgs.

* cited by examiner

POST-CRIMPING INSPECTION OF SCAFFOLDS MOUNTED ON SCAFFOLD DELIVERY SYSTEMS

BACKGROUND OF THE INVENTION

1. Field of the Invention

The present invention relates to drug-eluting medical devices; more particularly, this invention relates to systems, apparatus and methods for mounting to a delivery balloon a balloon-expandable scaffold, such as a polymeric scaffold.

2. Background of the Invention

FIGS. 1A and 1B depict perspective views of a prior art crimping station used to crimp a balloon expandable scaffold to a deployment balloon of a balloon catheter. The crimping station includes a crimper head 220, an interactive screen 216 for programming a crimping sequence, e.g., diameter reduction, dwell times between successive crimps, temperature control of the crimper jaws, etc. A carriage 242 aligns a catheter 209 with the opening 222 to the crimper head 220 and advances the distal end 209b of the catheter, where a scaffold 100 and the balloon are located, into the crimper head 220. The crimper head 220 includes three rollers 223, 224 and 225, which place a clean sheet of non-stick polymer material between the crimper jaws and scaffold 100 to avoid buildup of coating material on the jaws when plural scaffolds having drug-polymer coatings are being crimped to balloon catheters.

FIG. 1B shows a perspective view of the carriage 242, which includes a slidable block 250 holding catheter 209. The block 250 is used to advance the catheter distal end 209b and scaffold 100 into and out of the crimper head 220 using knob 274. The catheter 209 is held within a groove 252 formed on the block 250. The catheter 209 shaft is retained in the groove 252 by a pair of cylindrical rods 253, 254 which are rotated down to trap the catheter shaft in the groove 252 before it is advanced into the crimper head 220 via the opening 222. The rods 253, 254 are rotated from the closed position (as shown) to an open position to allow the catheter 209 to be removed from the groove 252 by rotating hinge arms 253a, 254a clockwise (as indicated by A, B). A handle 255 is connected to the hinge arms 253a, 254a and rotated in direction C to move the hinge arms 253a, 254a to the open position. A rail 273 is connected to the block 250 at block extension 250a. The block 250 is displaceable over a distance "S". An operator manually moves the distal end 209b and scaffold 100 towards or away from the crimper head 220 using the knob 274. The rail 273 is received within, and slides over a passage of a support 272, which is mounted to the table of the crimper station. The block 250 is received within, and slides along grooves (not shown) of a support piece 260. An abutment 275 of the support piece 260 serves as a stop to indicate when the catheter distal end 209b is positioned properly within the crimper head 220.

In operation, the operator manually places the catheter 209 within the groove 252 and holds it in place by rotating the handle clockwise to position the rods 253, 254 into the position shown in FIG. 1B. The operator then manually places the scaffold 100 over the balloon. Prior to inserting the distal end 209b within the crimper head 220, the operator must ensure that the scaffold is properly positioned on the balloon, i.e., the operator must ensure that the scaffold is located between marker bands of the balloon before placing the scaffold within the crimper head 220, so that when the balloon is inflated, the scaffold will expand properly within a patient's vasculature. The scaffold and balloon are then advanced into the crimper head by push the carriage forward until block 250 strikes or abuts the stop 275. When the block 250 hits the stop 275 the scaffold and balloon are in the desired position within the crimper head.

Preparing a scaffold-catheter assembly utilizing equipment such as that described above, and/or production techniques whereby operators dedicated to manually loading a scaffold on a balloon and ensuring the assembly is positioned/aligned properly so that the scaffold is properly crimped to the crimping head, is burdensome. In the case of high volume polymer scaffold—catheter assembly production there can be significantly more time spent properly crimping a polymer scaffold compared to a metal stent. Moreover, existing procedures for placing and aligning a scaffold, just prior to crimping has become more problematic and time-consuming as the lengths of deployment balloons have been shortened to about the length of a scaffold. Since the balloon length is matched more closely to the length of the scaffold (for purposes of avoiding damage to vascular tissue when the scaffold is deployed within a body) there is less margin for error by the operator. Given the small sizes for scaffolds and balloons, great care must therefore be exercised by the operator to ensure that the scaffold is properly located on the balloon before crimping. If the scaffold is not properly positioned on the balloon before crimping, both the scaffold and catheter must the discarded.

The art recognizes a variety of factors that affect a polymeric scaffold's ability to retain its structural integrity when subjected to external loadings, such as crimping and balloon expansion forces. These interactions are complex and the mechanisms of action not fully understand. According to the art, characteristics differentiating a polymeric, bio-absorbable scaffold of the type expanded to a deployed state by plastic deformation from a similarly functioning metal stents are many and significant. These and related challenges faced in the manufacture and crimping of polymer scaffolds to balloons are discussed in U.S. application Ser. Nos. 12/776,317 and 12/772,116.

One aspect of polymer scaffolds, as compared to metal stents, that has presented certain challenges is the procedures required to ensure an acceptable yield when crimping large numbers of polymer scaffolds to balloon catheters, as explained in more detail in US20120042501, U.S. application Ser. Nos. 12/776,317 and 12/772,116, as well as improving efficiency in crimping large numbers of polymer scaffolds to balloons so that production-level polymer scaffold crimping does not impose unacceptable delays in the manufacturing process. The operation of crimping devices are time consuming when being used to crimp polymer scaffolds and current production yields are less than favorable. Additionally, inspection of medical devices to ensure appropriate product quality requires some destructive testing, especially when a process is established for producing large numbers of such devices, a processing step is modified or when a device is first being mass produced. In the case of polymer scaffolds, this aspect of product development is particularly time consuming and expensive, not only due to the relatively new introduction of crimped polymer scaffolds and concomitant unknowns but also the relative complexity of polymer scaffolds (compared to metal stents) when crimped to and then later expanded from a balloon. As such, there is expected to be a relatively high level of destructive testing needed to ascertain whether a crimped scaffold will perform as intended when deployed within the body or when a crimp processing step is modified.

In view of the foregoing, there is a need to improve upon existing crimping processes, such as in the case of crimping polymer scaffolds to balloon catheters, including process control, modification of crimping processes and assessment of a manufacturing process.

SUMMARY OF THE INVENTION

The invention provides an apparatus, system and process for crimping a scaffold to a balloon catheter, and collecting data relating to a crimping process to ascertain by way of inspection of crimped scaffolds during the crimping process the suitability or effectiveness of crimping process parameters.

According to one aspect of the invention, a crimping system includes a computer control system and instrumentation that enables the monitoring of key process inputs and outputs by the crimper. The monitoring of key process inputs and outputs enables the ability to determine what process input conditions result in what process output attributes for the crimped stent or scaffold. The key process inputs have been determined to include time, temperature, pressure, speed, target diameter and target position. The key process outputs have been determined to include actual diameter, actual position and any crimping anomalies such as overlapping struts, bent struts, indentations and fractures. A crimper can be designed with a computer control system, software and instrumentation such as thermocouples, pressure transducers, servo motors/encoders and a camera-based vision inspection system to monitor process inputs and measure key process output attributes. Data collected from process cycles can be statistically analyzed to determine a range of process inputs that result in desirable process outputs. The establishment of these statistically valid relationships will allow fewer samples to be destructively tested to demonstrate sufficient control over the manufacturing process saving time and money. In addition, the integration of process input/output monitoring and analysis into the crimping equipment design will allow for timely feedback for process correction and optimization. A crimper designed with an integrated camera-based vision inspection system will allow images to be taken of the parts immediately before and after the crimping process. There is a significant advantage of performing the image acquisition and analysis immediately after the crimping process. The part is still under the automated control of the handling system and is untouched by human hands or other objects that could alter the condition of the part. In addition, in the case of a polymer scaffold, the crimped scaffold recoils causing the OD to increase as a function of time after removing it from the head. While under automated control, the OD measurement can be done at the exact same time after removal from the head resulting in a more representative measure of the process performance.

In one embodiment the crimper enables the collection of data about a scaffold, its delivery balloon and the state of the scaffold and balloon from the time the scaffold and catheter is loaded into the crimping system, through the final crimp and prior to placing a restraining sheath over the scaffold. In one particular embodiment a crimping system is used to crimp a scaffold made from a polymer comprising PLLA. Prior to crimping, the scaffold has a diameter about equal to, or greater than the scaffold's intended deployed diameter within a lumen ("deployed diameter" meaning about the diameter of the balloon when fully inflated). The scaffold's pre-crimp diameter can be 2, 2.5, 3, 3.5 or greater than its fully crimped diameter. As such, when the scaffold is crimped to the balloon and then removed from the crimper head there is a relatively large amount of recoil expected unless a restraining sheath is immediately placed over the scaffold, e.g., within less than 30 seconds, one minute, 1 minute, 2 minutes. For scaffolds deployed to higher diameters (compared to the crimped diameter) the amount of recoil expected can be higher and period of time permitted before a restraining sheath should be placed over the scaffold correspondingly less (other factors related to the material properties will of course also influence the recoil characteristics). According to the embodiments of scaffolds deployed to 2, 2.5, 3.0 and 3.5 as disclosed herein the sheath is placed over the scaffolds within 30 sec, 60 sec, within 30-60 sec, less than one minute, or less than two minutes after the scaffold is removed from the crimp head. According to the embodiments, a scaffold outer diameter is measured, or alignment of scaffold-balloon measurement is taken within 30-60 seconds, in less than 2 minutes, or less than 1 one minute after the scaffold is removed from the crimp head.

Examples of restraining sheaths for scaffolds are described in U.S. application Ser. No. 13/708,638. As such, there is no ability for a manual inspection of this type of crimped scaffold before a sheath must be fit over the scaffold to reduce recoil. Unless this recoil is restricted, the scaffold-balloon retention force will diminish and the crossing profile of the scaffold delivery system will increase.

The crimper system of the invention addresses the need for collecting data relating to a crimping process and prior to placing a restraining sheath over the crimped scaffold by incorporating an automated scaffold handling system and camera-based inspection system capable of collecting critical information about the scaffold and balloon prior to placing a restraining sheath over the scaffold. Such critical information may include a crimped scaffold outer diameter, the average and standard deviation of the outer diameter along the length of the crimped scaffold, the location of the scaffold end rings relative to the catheter marker bands and thus relative to the balloon tapers, the uniformity of balloon folds (as a way of predicting the degree of uniform expansion that will occur when the scaffold is deployed), crack propagation or fracture present in scaffold struts, uniformity of the compressed rings and crown angles lengthwise over the scaffold, flipping or overlapping struts, etc.

According to one aspect of the automated system, scaffold position relative to markers is recorded and then compared to a specification. This scaffold location will be a variable measurement data and not just pass/fail attribute data, in some embodiments, so that one can understand the effect of a scaffold location on product performance and use this data to optimize a specification to maximize yields while not compromising product performance. Through this process there can be a significant increase in yields. In other embodiments the automated process can include a pass-fail criteria, e.g., the relative position of distal or proximal end of a scaffold relative to a marker band is measured from an image, and if that number is greater than a predetermined number the scaffold is rejected, otherwise the scaffold is accepted. A similar pass/fail criteria may be developed based on a measured outer diameter.

An additional advantage of the crimper system is that more accurate assessments may be made about crimping processing parameters since the entire crimping process involves no manual manipulation of a scaffold or balloon by technicians. Accordingly, more accurate statistics of an influence or contributing factor to variances or changes in scaffold strength, integrity, balloon folding, etc. resulting from a modification of a processing parameter can be made. This is expected to lead to less of a need to perform destructive testing, such as when a relatively minor change is made in a processing parameter.

According to another aspect of the disclosure, a scaffold mounting system includes a crimper head and a pair of stations, located on opposite sides of the crimper head, for positioning first and second scaffold and catheter assemblies and aligning the first and second scaffolds on their respective balloon catheters prior to crimping the scaffolds to the balloons. The crimper head is adapted for receiving the scaffold and catheter assemblies from both stations to perform a crimping process at the same time. The system incorporates computer-controlled processes for reducing much of the labor typically required by an operator, e.g., a technician, when preparing a scaffold and catheter for crimping and monitoring the crimping process. Automated, computer-controlled processes replacing manual pre-crimping processes can increase yield, since there is less likelihood that a scaffold and catheter will be improperly located within the crimper head, which can result in uneven crimping over the length of a scaffold, or a scaffold not properly aligned with a balloon markers prior to crimping. By using automated, computer-controlled process the time required for crimping can be reduced, and production yields increased. Moreover, more operator time is made available, so that multiple crimping sequences can be monitored by the same operator.

These and other advantages of the invention are particularly worth noting when polymer scaffolds are crimped. In contrast to a metal stent, a polymer scaffold must be crimped at a much slower rate due to the inherent limitations of the material compared at that of a metal. This slower process can produce significant bottlenecks during scaffold-catheter production. By automating manual crimping tasks, the overall time needed to crimp a polymer scaffold can be noticeably reduced. Polymer scaffolds are more sensitive to fracture when crimping produces irregular bending or twisting of struts, since a polymer material suitable for a load-bearing scaffold, e.g., PLLA, is far more brittle than a metal. Inaccurate crimping within the crimper head, e.g., non-uniform applied forces through the crimper jaws when the scaffold and catheter are not properly located, or positioned within the crimper head, is therefore more likely to cause fracture in polymer scaffold struts. Accuracy and repeatability in the crimping process is therefore more critical to increased yield for a polymer scaffold than a metal stent. According to one aspect of the invention, there is a discovered need for more automation in a crimping process for polymer scaffolds, whereas there is less need for automation when crimping metal stents. A crimping sequence for a polymer scaffold can be about five times longer than a metal stent. This 5-fold increase in crimping time, when multiplied out by the number of polymer scaffold-balloon assemblies crimped during a production run, poses unique challenges in planning and resource allocation, which is contrast to the time and resource allocation needed for crimping metal stents. A primary reason for the delay is the need to crimp the polymer material more slowly to reduce instances of crack creation or propagation, and to reduce recoil when the crimping jaws are removed from the scaffold surface.

Existing systems for crimping a scaffold to a balloon require an operator to both manually align scaffolds between balloon markers, properly insert the scaffold and balloon assembly within a crimper head and then verify that the scaffold is being properly crimped in mid-process. The invention substantially overcomes many of the drawbacks of requiring an operator to perform these tasks by introducing automated processes for positioning and aligning a scaffold and catheter for crimping.

According to the disclosure, the system may be configured to automate the following manual tasks:

Manually positioning a catheter distal end at the entrance of the aperture and then manually advancing the scaffold and catheter within the crimper head. According to one aspect of the invention, a computer automatically advances the scaffold and catheter into the crimper head after an operator has verified, e.g., by a laser light identifying the proper location of the catheter's proximal balloon seal relative to a reference point, that the catheter has been properly placed within a carriage that advances the catheter and scaffold into the crimper head under computer control. A laser positioning system or a camera may be used to locate the proper placement of the catheter relative to the carriage, as well as to signal to a processor controlling the carriage motion forward into the crimper head that the scaffold-catheter as been positioned properly within the crimper head, once this signal is received, an actuator advances the scaffold-catheter assembly into the crimper head. The device illustrated in FIGS. 1A-1B, by contrast, utilizes a mechanical stop 275 to indicate to the operator that the scaffold-catheter assembly is located properly within the crimper head. However, it has been discovered that this manner of positioning the scaffold-catheter assembly within the crimper head can cause the scaffold to displace relative to the balloon, thereby throwing the scaffold out of alignment. The invention recognizes that a mechanical stop, even when found suitable for positioning a metal stent within a crimper head, introduces problems for polymer scaffolds, particularly when the polymer scaffold has a much larger diameter than the balloon. As a solution to this problem, a servo mechanism is used to advance the scaffold-catheter assembly into the crimper head at a rate which reduces the chance that the scaffold will move relative to the balloon.

Manually aligning the scaffold between balloon markers. According to one aspect of the invention, an imaging system is used to image the scaffold and catheter and then determine, e.g., by pattern recognition software, whether the scaffold is properly aligned. If the scaffold is not properly aligned, the scaffold position relative to balloon markers is adjusted using computer-controlled actuators. The actuators may be controlled by servo mechanisms driven by a processor, which processor may utilize a camera or laser alignment system and may incorporate controller logic with or without a feedback loop during the adjustment.

Manual inspection of the scaffold on the balloon after an initial, or pre-crimp, to ensure that the scaffold has not shifted relative to the balloon markers within the crimper. If the scaffold has shifted, then the operator manually adjusts the scaffold before placing the scaffold and catheter back into the crimper. According to another aspect of the invention, the crimping process is under computer control after the scaffold-catheter assembly is loaded onto a carriage and the operator activates the process. The scaffold-catheter assembly is placed in the crimper head, a pre-crimp is performed, then the scaffold-catheter are withdrawn from the crimper head. The imaging system is then activated to verify that the scaffold is aligned with the balloon markers. After verifying that the scaffold is between the balloon markers, the scaffold-catheter assembly is advanced again into the crimper head to perform the final crimp. No operator involvement is necessary.

Performing the above manual processes, one after another, for a first scaffold, then a second scaffold after the first scaffold has been crimped to a balloon. According to another aspect of the invention, a crimper head is provided for simultaneously crimping first and second scaffold and catheter assemblies in one crimping sequence. Hence, the automated positioning, aligning, and verification after pre-crimp steps described above can be performed concurrently for two scaffold and catheter assemblies.

The invention addresses the need to improve alignment processes for scaffold-catheter assemblies that demand tighter alignment tolerances. Short balloon tapers and shorter balloon marker bands drive more precise scaffold positioning on the balloon. Precise position correction of the scaffold is difficult to perform manually by an operator and requires special training. Manually positioning can result in scaffold, coating and/or balloon damage if not done correctly. This positioning task is made more difficult when the scaffold is manufactured to have a deployed or over-deployed diameter (a large starting diameter is chosen to provide improved mechanical characteristics when the scaffold is expanded to its deployed diameter). The relatively large annular gap between the scaffold and folded balloon presents significant positioning challenges.

Consistent with these objectives and in view of the foregoing problems and/or needs in the art addressed/met by the invention, in one aspect, a method for crimping a scaffold to a balloon catheter includes connecting the scaffold and balloon catheter to a member including an actuator capable of rotating a distal end of the balloon catheter about a longitudinal axis and inserting the distal end into and removing the distal end from a crimper head, the crimper head configured for crimping the scaffold to the balloon; inserting the balloon and scaffold into the crimper head using the actuator; crimping the scaffold to the balloon to produce a crimped scaffold; removing the crimped scaffold from the crimper head using the actuator; collecting images of the crimped scaffold and balloon using the actuator to displace and/or rotate the scaffold about the longitudinal axis; and after collecting images, placing a restraining sheath over the crimped scaffold.

In another aspect there is a method of crimping a scaffold to a balloon of a balloon catheter, comprising placing the scaffold in a receptacle, engaging the catheter by an arm; inserting the balloon at least partially within the scaffold using the arm being displaced by a motor; positioning the scaffold on the balloon by either of pulling a distal end of the balloon towards a distal end of the scaffold, or pushing the distal end of the scaffold towards the distal end of the balloon using the arm being displaced by the motor; and crimping the scaffold to the balloon.

In another aspect there is an apparatus for mounting a scaffold to a balloon catheter, comprising: a crimper head having jaws and configured to crimp the scaffold to a balloon of the balloon catheter; an actuator including a motor capable of rotating a distal end of the balloon catheter about a longitudinal axis and inserting the distal end into and removing the distal end from the crimper head; an imaging device; a processor; and machine executable code, executable by the processor, for performing a mounting process, the machine executable code including a first code for causing the actuator to translate and/or rotate about the longitudinal axis; a second code for crimping the scaffold to the balloon using the crimper head; and a third code for collecting images of the crimped scaffold.

In another aspect there is a method for evaluating a crimping process parameter, comprising: providing a crimping apparatus including a crimper head and an automated control actuator capable of placing a scaffold and a balloon of a balloon catheter into and removing the scaffold and the balloon from a crimper head, and obtaining images of the scaffold and/or balloon, where in the crimping apparatus is configured for crimping a scaffold to a balloon according to process parameters including scaffold temperature, balloon pressure, crimp time, crimp speed, and target diameter; providing first and second process parameters for crimping, each of the first and second process parameters specifying one or more of a scaffold temperature, balloon pressure, crimp time, crimp speed, and target diameter for crimping, wherein the respective one or more of the scaffold temperature, balloon pressure, crimp time, crimp speed, and target diameter is not equal between the first and second process parameters; crimping a first plurality of scaffolds to balloons using the first process parameters including placing a sheath over each of the crimped scaffolds to minimize recoil, and obtaining a first plurality of images of each of a respective first plurality of crimped scaffolds and/or balloons before the sheath is placed over the crimped scaffold; crimping a second plurality of scaffolds to balloons using the second process parameters including placing a sheath over each of the crimped scaffolds to minimize recoil, and obtaining a second plurality of images of each of a respective second plurality of crimped scaffolds and/or balloons before the sheath is placed over the crimped scaffold; comparing the first plurality of images to the second plurality of images showing crimped scaffolds without a sheath including generating a number indicating whether the first or second process parameters produces one or more of less variance in scaffold crimped diameter, more uniformity in balloon folds, less cracks, or overlapping struts in a crimped scaffold.

The invention further provides a crimper head, a first station and a second station disposed adjacent the crimper head and configured to receive, respectively, a first scaffold and a first balloon catheter assembly and a second scaffold and a second balloon catheter assembly, the first station and the second station each include an aligning portion and a positioning portion, and a processor for simultaneously crimping both the first scaffold to the first balloon catheter and the second scaffold to the second balloon catheter using the crimper head. When a user command, e.g., start crimping sequence, is received by the processor, the processor, e.g., a local computer, causes (a) the first station to align the first scaffold with the first balloon catheter and the second station to align the second scaffold with the second balloon catheter using the respective first and second station aligning portions, (b) the first station to insert the first scaffold and first balloon catheter into the crimper head and the second station to insert the second scaffold and second balloon catheter into the crimper head using the respective first and second station positioning portions, and (c) the crimper head to perform a crimping sequence for crimping both the first scaffold to the first balloon catheter and the second scaffold to the second balloon catheter.

According to another aspect of the invention, there is provided machine executable code residing on a machine readable storage medium for performing tasks (a), (b) and (c). The machine readable code may include code for operating the aligning portion using a control system (with or without a feedback loop).

The aligning portion may include a camera for obtaining an image of a scaffold on a balloon, machine readable instructions accessible to the processor for analyzing the image to determine whether the scaffold is misaligned on the balloon, an actuator for displacing one of the scaffold and balloon relative to the other of the scaffold and balloon if a misalignment of the scaffold relative to the balloon was detected from the analyzed image, and a controller for controlling movement of the actuator for displacing one of the scaffold and balloon relative to the other using the actuator according to an offset of the scaffold relative to the balloon.

According to another aspect of the invention, there is a method for crimping a scaffold to a balloon of a balloon catheter, the balloon having balloon markers identifying a proper alignment of the scaffold with the balloon, the method including preparing the balloon catheter for crimping including placing the catheter on a movable carriage; verifying that the scaffold is aligned with the balloon including collecting at least one image of the scaffold and balloon and then analyzing the image to verify that the scaffold is between the balloon markers; after the verifying step, inserting the scaffold and balloon into a crimper; and crimping the scaffold to the balloon.

According to another aspect of the invention, there is a crimping method for a polymer scaffold including a final crimp followed by a dwelling period. During the dwell period the balloon and scaffold are maintained at an elevated temperature and a leak test for the balloon is performed while the scaffold-catheter assembly is being gripped by the crimper jaws.

According to another aspect of the invention, there is an apparatus for crimping a polymer scaffold to a balloon catheter, comprising: a crimper head having jaws; an aligning portion; a positioning portion; a processor in communication with the crimper head, aligning portion and the positioning portion; and machine executable code, executable by the processor, for performing a crimping process.

The machine executable code includes a first code for aligning the polymer scaffold with the balloon of the balloon catheter and positioning the polymer scaffold and balloon within the crimper head, and a second code for crimping the polymer scaffold to the balloon, including setting the crimper jaws at a final crimping diameter followed by a dwell time to allow stress relaxation to occur within the polymer scaffold and to perform a balloon test including inflating the balloon to a pressure and then measuring the pressure over a time period to detect a leak in the balloon.

According to another aspect of invention, one or more crimping process parameters specifying one or more of a scaffold temperature, balloon pressure, crimp time, crimp speed, and target diameter for crimping are evaluated using a camera based inspection system included with a crimper to determine the degree that changes in one or more of the process parameters effects changes in crimper diameter, balloon folds, uniformity of crown angle, diameter of each ring, strut overlapping, crack propagation and recoil.

According to another aspect of invention there is a method for crimping including placing a scaffold on a balloon, crimping the scaffold including performing a leak test, removing the scaffold from the crimper, generating images of the scaffold and placing a sheath over the scaffold after generating the images.

According to other aspects of invention there are the following features taken separately and individually or in any combination of the following: a method for crimping that generates a pass-fail signal when a crimped scaffold is not aligned with a balloon marker; a measurement of a scaffold outer diameter and/or balloon marker alignment by an automated process and/or prior to placing a sheath over the scaffold; a crimper apparatus that one or both measures a crimped outer diameter and balloon alignment using a servomechanism and camera; a software product including non-volatile information stored on a computer-readable medium, the data including images of a crimped scaffold, and a measurement of an outer diameter logically structured in relation to crimping process parameters and information on functional testing of the crimped scaffolds; a database structured in a logical ordering functional outputs such as deploy to fracture or acute recoil to crimping process parameters; a non-transitory computer-readable media having computer-executable instructions embodied thereon that, when executed by a computing device having a processor, perform a method of crimping including applying crimping process parameters (e.g., temperature, rate, and others as set forth herein) to crimping using a crimp head, measuring the scaffold relative to the balloon, the scaffold attributes including the outer diameter, and generating images of the scaffold and/or balloon.

The scope of the methods and apparatus of the invention also encompass processes that crimp a scaffold as substantially described in US Pub. No. 2010/0004735, US Pub. No. 2008/0275537, and US Pub. No. 2012/0010693.

The thickness of the tube from which the scaffold is formed may have a thickness of between 0.10 mm and 0.18 mm, and more narrowly at or about 0.152 mm. The scaffold may be made from PLLA. And the scaffold may be crimped to a PEBAX balloon.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

DETAILED DESCRIPTION OF EMBODIMENTS

Throughout this disclosure, the balloon expandable implant will be called a "scaffold", whether the description is referring to an implant made in whole or part of a metal material or a bioresorbable or biodegradable polymeric material, such as PLLA, or a biodegradable metal. In some instances, the term "scaffold" may be used, which is specifically referring to a biodegradable or bioresorbable polymer implant. "Stent" refers to a non-biodegradable or non-bioresorbable implant, unless indicated otherwise.

Figure 2:
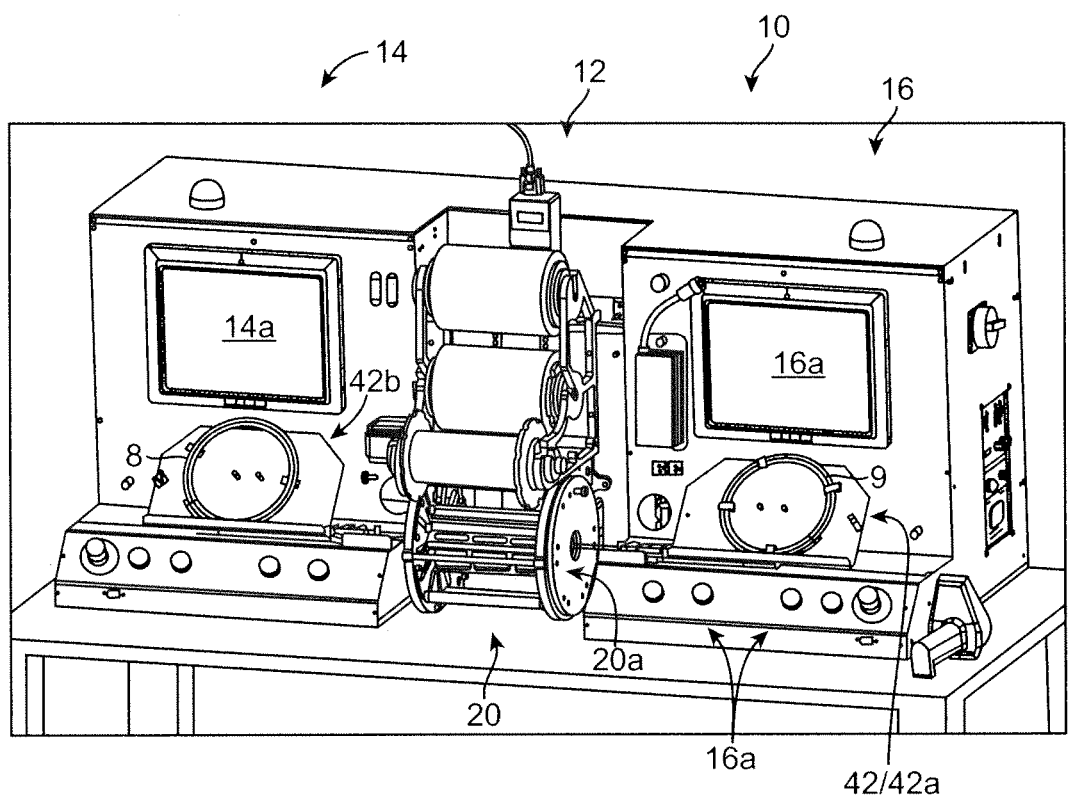
FIG. 2 is a perspective view of a scaffold mounting system configured for positioning and aligning two pair of scaffold-catheter assemblies at stations on left and right sides of a crimper head and then crimping the scaffolds to their respective catheters using the crimper head, and using a single crimping cycle. In one aspect of the disclosure, the process is automated, involving little if any operator involvement once the scaffold-catheter assembly has been placed on carriages at the left and right sides of the crimper head.

FIG. 2 illustrates a scaffold mounting system 10 according to one aspect of the disclosure. The scaffold mounting system 10 is configured for positioning a scaffold on a delivery balloon, then crimping the scaffold to the balloon in an automated fashion. The system 10 is preferably constructed so that two scaffolds may be simultaneously loaded onto separate balloon catheters, then each placed within a crimper head by a computer-controlled positioning and alignment system. Both scaffolds are then crimped to their respective balloon using the same crimper head. As such, two scaffolds may be simultaneously crimped to catheters during a single crimping sequence. The attending operator need only perform a relatively straight-forward assembly of the scaffold and catheter, and then mount the scaffold-catheter assembly on a carriage. A start sequence button is pressed, at which point the remainder of the process is hands-off, thereby alleviating the operator from much of the manual labor that is typically required with existing systems.

Referring again to FIG. 2, system 10 includes left and right positioning and alignment stations 14, 16 located on left and right sides, respectively, of a crimping apparatus 12, which includes the crimping head 20, e.g., an iris-type crimper, and rollers for dispensing a thin sheet of a non-stick polymer material between jaws of the crimping head 20 and a scaffold to be crimped. Coiled catheters 8, 9 are shown mounted on respective computer-controlled left and right moving carriages 42a, 42b portions of the positioning and alignment stations 14, 16. The carriage portions 42a, 42b may perform various functions associated with an automated scaffold positioning and alignment process, such as positioning the catheter distal end (where the balloon is located) within the appropriate location in the crimping head 20 and aligning the scaffold on the balloon of the catheter prior to initiating a crimping sequence. After the scaffold is properly aligned relative to balloon markers, the catheter with scaffold is advanced into the crimper head 20 to start the crimping sequence. The scaffold may then be reduced in diameter to a final crimped state before being withdrawn from the crimper, or partially reduced in diameter, removed to verify proper placement on the balloon, then re-inserted into the crimper to complete the crimping process.

Figure 3:
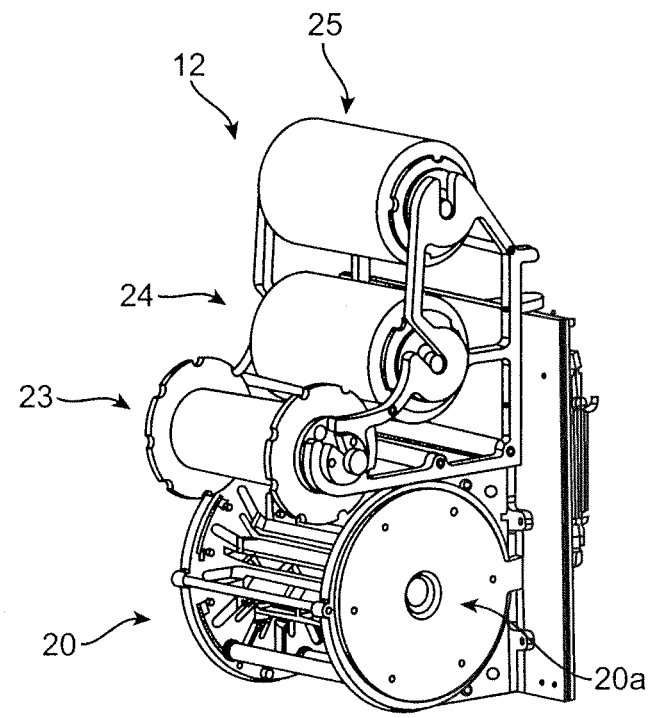
FIG. 3 is a perspective view of a mounting apparatus of the system of FIG. 2 including a crimper head and dispensing rolls.

Referring to FIG. 3, there is shown a perspective view of the mounting apparatus 12. As mentioned above, this portion of the mounting system 10 includes a crimper head 20 and dispensing rolls. The crimper head 20 may be an iris type crimper, an example of which is described in US Pub. No. 2003/0070469. The crimper head 20 includes left and right apertures for passage of the scaffold and catheter into the crimper head 20 via the left and right positioning and alignment systems 14, 16, respectively (aperture or opening 20a is viewable in the perspective views of FIGS. 2 and 3). Preferably, the crimper head 20 is configured with a compliance offset feature which allows it to properly crimp one or two scaffolds. The compliance offset feature may be implemented by an adjustment of the travel of the crimper jaws on one end when only one scaffold is being crimped. Without adjustment of jaw loading between two vs. one scaffolds being crimped at the same time, the crimper jaws will produce an uneven force distribution over the length of the scaffold.

One favorable aspect of a crimper head configured to simultaneously crimp two scaffolds as depicted in FIGS. 2 and 3 is uniformity of the applied load on the scaffolds and bearings of the crimper head. Scaffold designs can range from 8-80 mm and longer for some applications. Due to catheter fixturing limitations, the proximal edge of the scaffold is inserted the same distance into the crimp head for all scaffold sizes. The crimp head can experience high torsional loading in the bearings and diameter disparity between the right hand side and left hand side when a scaffold of short length is disposed on only one of these sides. By having scaffolds located on both sides of the crimper head the load becomes more evenly distributed, or balanced, thereby providing more uniform resistance during the crimp process.

Three rolls 23, 24, 25 are used to position a clean sheet of non-stick material between the crimping jaws and scaffold prior to crimping. For example, upper roll 25 holds the sheet secured to a backing sheet. The sheet is drawn from the backing sheet by a rotating mechanism (not shown) within the crimper head 20. The used sheet is gathered by the mid roll 24 after crimping and the backing sheet is collected by the lower roll 23. As an alternative to rollers dispensing a non-stick sheet, each scaffold may be covered in a thin, compliant protective sheath before crimping.

The dispensed sheet of non-stick material (or protective sheath) is used to avoid buildup of coating material on the crimper jaws for scaffolds coated with a therapeutic agent held within a polymer carrier. The sheet is replaced by a new sheet after each crimping sequence. By advancing a clean sheet after each crimp, accumulation of coating material from previously crimped scaffolds can be avoided. The film is also beneficial when crimping a polymer scaffold. When metal jaws of a crimper apply pressure to struts of a polymer scaffold, damage can occur to the struts due to the difference in hardness between the metal and polymer. The polymer film provides a more compliant surface between the jaws and the scaffold struts to avoid pitting of the scaffold struts during crimping.

Left positioning and alignment station 14 has the same characteristics as right station 16. Therefore, the remaining discussion applies to either station 14 or 16. Right alignment station 16 includes a display which may be an interactive display 16a for modifying, or simply monitoring a pre-programmed positioning and alignment sequence for a scaffold and catheter, and subsequent crimping sequence. Information about the process for the particular scaffold is retrievable from an input scaffold ID. After scanning in the scaffold ID via a barcode or receiving the scaffold ID via an RFID transmitter on the scaffold holder, the station 16 may upload from a remote storage area process information including parameters/recipes for crimping the particular scaffold to a catheter, e.g., balloon pressures, dwell times, diameter reductions, temperature, etc. Additional information may be uploaded from the scaffold ID, such as scaffold and balloon sizes, which additional information is used to assist with an automated alignment of the scaffold on the catheter, discussed below.

Control buttons 16a on the front panel of the station 16 may be provided to initiate or abort intermediate phases of a crimping process, e.g., control buttons for initiating/aborting an alignment of the scaffold on catheter, clamping or releasing the catheter to/from the carriage 42a, aborting a crimping step, advancing the scaffold and catheter into, or removing the scaffold and catheter form the crimper head 20, etc.

As indicated above, a polymer sheet is disposed between the scaffold and crimper jaws. It has been found that a significant static charge can be present on these sheets. Additionally, a static charge can build up when the polymer scaffold is slid over the balloon surface, or during pre-handling of the scaffold. For a polymer scaffold having a much larger diameter than the balloon, these static charges can cause the scaffold to be thrown out of alignment, either when resting on the balloon or when the scaffold-catheter assembly is initially introduced to the crimper head and in proximity of the charged polymer sheets. For a polymer scaffold crimping process, it is desirable to remove or minimize this static charge prior to inserting the scaffold-catheter assembly into the crimper head. For example, anti-static air may be directed into the crimper head and over the scaffold-catheter assembly prior to crimping.

Figure 4A:
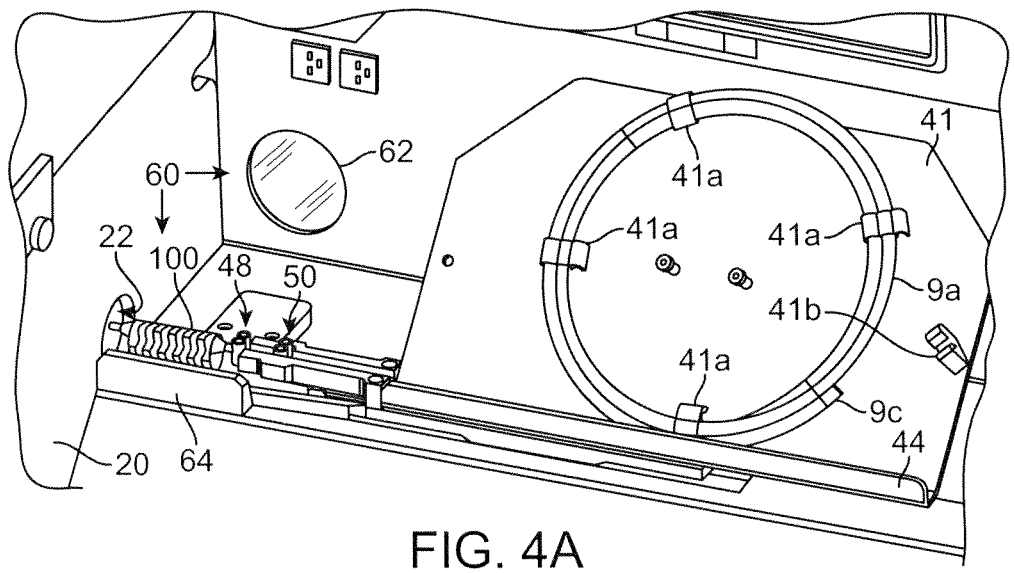
FIGS. 4A-4B are close-up views of a positioning and alignment system for the right hand side station of the system of FIG. 2. Shown are elements of an imaging system and a carriage associated with a positioning and alignment system.
Figure 4B:
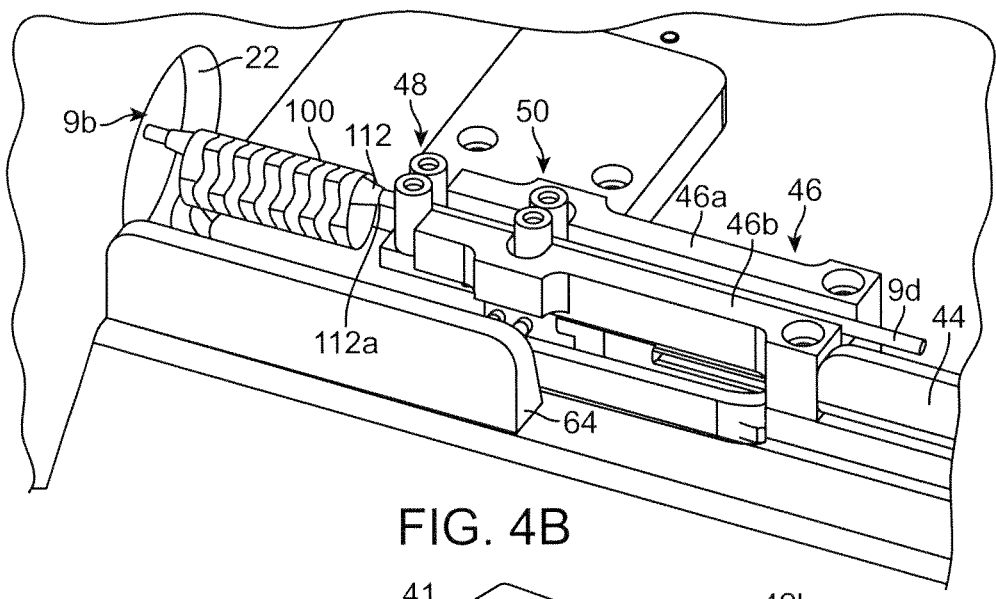

Station 16 includes a carriage 42a (hereinafter carriage 42 or 42a), which carries the scaffold and catheter into and out of the crimper head 20 and assist with re-aligning the scaffold 100 on the balloon 112. The carriage 42 translates left and right by a computer-controlled, linear drive mechanism coupled to the carriage 42. Referring to FIGS. 4A-4B there are two close-up perspective views of right positioning and alignment station 16, in particular, the carriage 42 and elements of an imaging system 60 (a camera 62 and reference plane 64) which are used with the carriage 42 to assist with aligning the scaffold 100 on the balloon 112. The carriage 42 includes a tray 41 for holding a coiled portion 9a of the catheter 9 (via clips 41a). The tray 41 includes a proximal guiding flange 44 which directs the catheter 9 shaft towards fore and aft grippers 48, 50 disposed adjacent a channel 46 for holding the distal end 9b of the catheter 9 in alignment with the entrance 22 to the crimper head 20. The proximal end 9c of the catheter 9 is disposed in a convenient position on the tray 41 to attach a luer extension, which provides a coupling for connecting a pressure source (not shown) and associated pressure gauge to the distal catheter end 9c. The pressure source and gauge are placed in fluid communication with the balloon inflation lumen for inflating and measuring balloon pressure when the scaffold-catheter assembly is within the crimper head 20. A clip 41b is provided for attaching a hose, which couples to the luer extension.

The carriage 42 channel 46 includes an outer channel piece 46b and inner channel piece 46a, arranged to form parallel walls for alignment of the catheter 9 shaft 9d with the crimper head 20 entrance 22. The distal gripper pair 48 and proximal gripper pair 50 include a pair of opposed posts each receiving a compliant sleeve that abuts the catheter shaft. The distal grippers 48 are fixed in position and spaced apart to provide a snug space for the catheter distal end 9b. The proximal gripper pairs 50 are movable towards and way from each other by a pneumatic actuator to secure and release, respectively, the distal catheter shaft 9d from the channel 46. A user toggle switch (not shown) releases or engages the grippers 50 with the catheter shaft 9d. The grippers 50, therefore, operate as a clamp to hold the catheter 9 distal end 9d within the channel 46. The catheter 9 is positioned in the carriage 42 so that the balloon 112 is forward of the distal grippers 48. The scaffold 100 is on the balloon 112 in FIGS. 4A-4B. As an aid in alignment a metal rod (not shown) is advanced through the catheter guide wire lumen to increase the catheter's flexural rigidity at the distal end. The channel 46 includes a V-groove formed by a magnetic material, or having a magnetic material proximate the groove to bring the catheter into alignment within the groove and retain it in this position by magnetic forces acting on the rod disposed within the guidewire lumen.

The scaffold 100 may be manually placed on the balloon 112 by the operator after the balloon 112 has been positioned distal of the grippers 48. After the balloon 112 and scaffold 100 have been properly located on the carriage 42 distal of the grippers 48, the toggle switch is depressed to bring the proximal gripper pair 50 together to clamp the catheter 9 in place. In another embodiment, the scaffold may be placed on a tray and the catheter (held on the carriage 42) advanced through the scaffold bore by a computer-controlled actuator. This scaffold tray may have a curved receiving surface, e.g., a portion of a cylindrical surface, to receive the scaffold, which allows the operator to simply drop the scaffold onto the receiving surface where the receiving surface naturally causes the scaffold to come to rest at the center, e.g., scaffold bore axis and axis of cylinder lie in same plane. A flange may be formed along the distal edge of this receiving surface so that the scaffold abuts the flange if the scaffold is displaced distally. The catheter distal end is advanced into the scaffold bore until the distal balloon marker begins to appear distal of the scaffold distal end. If there is contact between the catheter and scaffold during this step, the distal flange will act as a stop to hold the scaffold in position while the catheter distal end is passing through the scaffold bore. In another example the tray depicted in FIG. 6 and described more fully below may receive the scaffold. Then the catheter distal end is advanced through the scaffold bore. In either of the above embodiments, e.g., tray of FIG. 6 or body having a curved receiving surface, the scaffold alignment process (as described in greater detail below) may be performed concurrently with placing the scaffold on the distal end of the catheter.

Figure 4C:
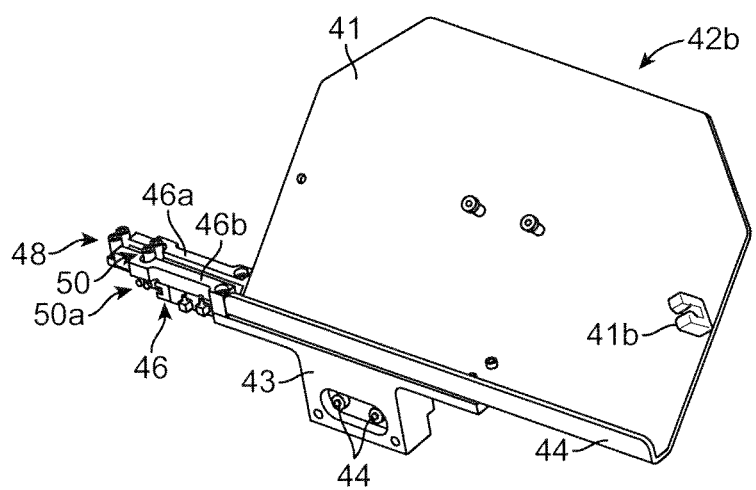
FIG. 4C is a perspective view of the carriage portion of the positioning and alignment system of FIG. 2.

FIG. 4C shows a perspective of the carriage 42. As mentioned above, carriage 42 includes a tray 41 with rail portion 44, rail 46 and clip 41b, and grippers 48, 50. In FIGS. 4A-4B carriage is shown being received within a slot which it translates along as the scaffold-catheter assembly is moved towards/away from opening 22. Carriage 42 includes an extension piece 43 received within the slot and connected to a linear actuator via bolts 44. Grippers 50, which are pneumatically actuated, are connected to the actuator via couplings 50a.

A laser light (or camera) may be used to assist the operator with identifying the appropriate position of the balloon 112 aft seal 112a relative to the distal gripper pair 48, to ensure that the balloon 112 and scaffold 100 will be advanced to the designated area within the crimper head 20 prior to activating the crimper head 20. If the catheter distal end 9b is too far forward of, or close to the gripper 48, which is arbitrarily chosen, for convenience, as the reference point for the travel length forward of the carriage 42 from the position shown in FIG. 4A to a crimping location within the crimper head 20, then the scaffold and catheter can be positioned incorrectly within the crimper head 20, resulting in possible damage to the scaffold and/or the crimper head. The operator adjusts the position of the catheter distal end 9b relative to the laser light, which is directed at, and generates a red line across the catheter shaft, until the balloon 112 proximal seal 112a is illuminated by the light. This laser light is directed about 10 mm forward of the grippers 48.

As mentioned earlier, the carriage 42 and imaging system 60 assist with aligning the scaffold on the balloon. As shown in FIG. 4A, the catheter balloon 112 and scaffold 100 are located between the reference plane 64 and the camera 62 (the reference plane provides a black backdrop, or contrasting background to the scaffold and catheter so that images collected by the camera 62 can clearly discern the scaffold and balloon 112 distal and proximal seals, and/or balloon markers). The background may be any color or may consist of another light source to backlight the product if desired for accurate dimensional transitions.

Reference points may be disposed on the backdrop or contrast surface, e.g., an approximate distal and proximal location for the balloon on the catheter when the balloon has properly positioned on the rail by the operator, or reference indices indicating a measure of length, e.g., hashes showing millimeter increments.

After the catheter 9 is positioned in the carriage 42 as shown in FIG. 4A, scaffold 100 alignment on the balloon 112, followed by the crimping sequence may be initiated by an automated process. Thus, following proper placement of the catheter 9 within the carriage 42, the remainder of the crimping process for the scaffold 100 and catheter balloon 112 may commence without further involvement by the operator.

Misalignment of the scaffold on the balloon may be detected using the imaging system 60 and computer-executed algorithm that includes a position detection routine that collects digitized image(s) of the scaffold 100 on the balloon 112 and analyzes the image(s) to determine whether the scaffold is aligned or misaligned. That is, collected image(s) is/are analyzed to locate edges 104, 105 of the scaffold relative to the balloon 112 (see FIG. 5A). To assist with identification of scaffold edges, balloon seals, scaffold and balloon markers etc. from the images data about the scaffold is accessed. Scaffold and balloon lengths, distances from edges to markers, etc. and other identifying characteristics may be remotely accessed through the scaffold ID then compared to the image to identify (through pattern recognition routines) the scaffold structure used to determine whether the scaffold is misaligned relative to balloon markers 114.

After a determination has been made that the scaffold is misaligned, a positioning mechanism is employed to automatically reposition the scaffold 100 on the balloon 112. The computer algorithms that may be used to re-align the scaffold include a controller with or without a feedback loop. In both instances, the controllers seek to move the scaffold by a computed offset distance to properly align the scaffold between balloon markers.

Figure 5A:
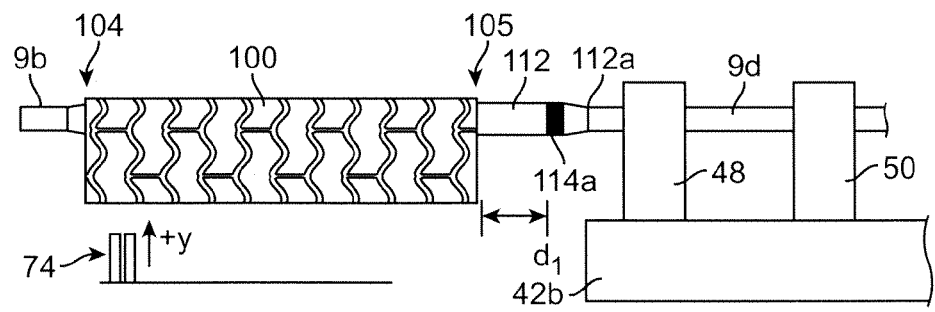
FIGS. 5A-5C is a sequence of views showing a re-positioning/re-alignment of a scaffold on a balloon. The sequence shown uses computer-controlled actuator portions of the positioning and alignment system.

For example, referring to a controller without feedback, after locating the scaffold edges 104, 106, balloon seals 112b, 112a and/or marker bands 114a, 114b in the image, the scaffold 100 position relative to the balloon markers can be found and an offset distance "d1" computed (FIG. 5A). This offset is then input to the controller that has control over movement of carriage 42 and/or scaffold 100 to move one relative to the other. After the balloon 112 has been displaced relative to the scaffold 100, or the scaffold 100 displaced relative to the balloon 112, presumably by the distance d1, a second image is taken to re-evaluate the scaffold position relative to the balloon 112. The same sequence may be performed multiple times until the scaffold 100 is properly located on the balloon 112, e.g., between marker bands 114a, 114b. Movement of the scaffold relative to the balloon is determined once the offset d1 is computed. If the second image reveals that the scaffold is still misaligned, a new offset d1 is computed and the process is repeated.

Examples of actuator-controlled mechanisms that may be incorporated into station 16 for restraining or moving the scaffold relative to the balloon 112 (or balloon relative to scaffold) are depicted in FIGS. 5A-5C, FIG. 6 and FIGS. 7A-7B.

Figure 5B:
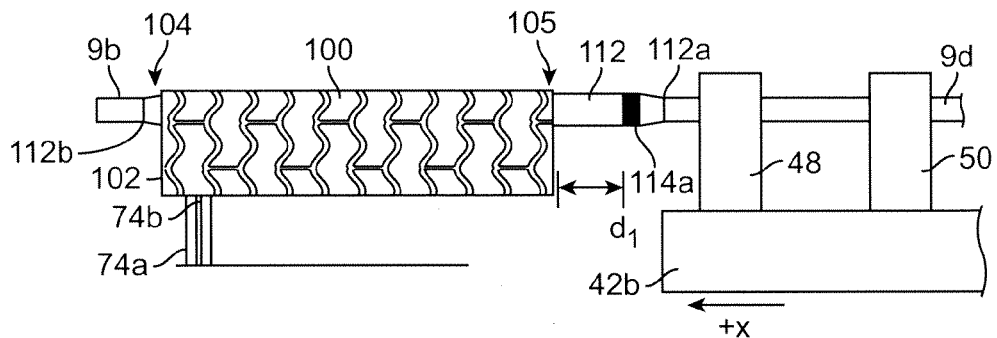
Figure 5C:
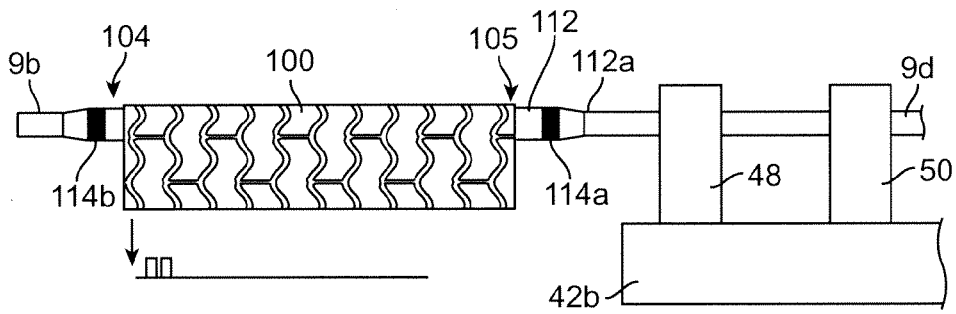

Referring to FIGS. 5A-5C, located beneath the scaffold 100 is an arm or pair of arms 74 that are raised (+y) to engage struts or ring elements of the scaffold 100. Shown is one pair of arms 74 at end 104 of scaffold 100. The arms 74a, 74b are positioned between a scaffold strut and then brought together to grip the strut or ring element 102 (FIG. 5B). Or the arms 74a, 74b may be positioned between struts and then moved apart until then contact a scaffold ring element or strut. Two pair of arms of the type shown (i.e., arms 74), operated simultaneously, may restrain both ends 104 and 106 of the scaffold, or one arm (or post) at each end 104, 106 may be raised (+y) to serve as an abutment preventing horizontal motion (+/−x) of the scaffold 100 relative to the balloon 112 so that the balloon 112 may be moved relative to the scaffold 100. Referring to FIGS. 5B-5C, the carriage 42, for example, is moved forward by the distance d1 while the scaffold is held by the arms 74. After the carriage 42 is moved, the arms 74 are retracted to their starting position. A second image of the scaffold 100 and balloon 112 is taken to determine whether the scaffold 100 is now located between the marker bands 114a, 114b as shown. Referring of FIG. 6, a cradle 76 having a plurality of upwardly disposed protuberances 77 (e.g., square-like extensions, bumps) or roughened (rubber like) surfaces 77 having a high coefficient of friction may, in the alternative, be used to restrain scaffold 100 motion while the balloon 112 is repositioned. Alternatively, the cradle 76 may be moved horizontally (−x) to move the scaffold 100 relative to the balloon 112. This tray 76 may also be used to place the scaffold 100 on the catheter 9, as mentioned earlier.

Figure 7A:
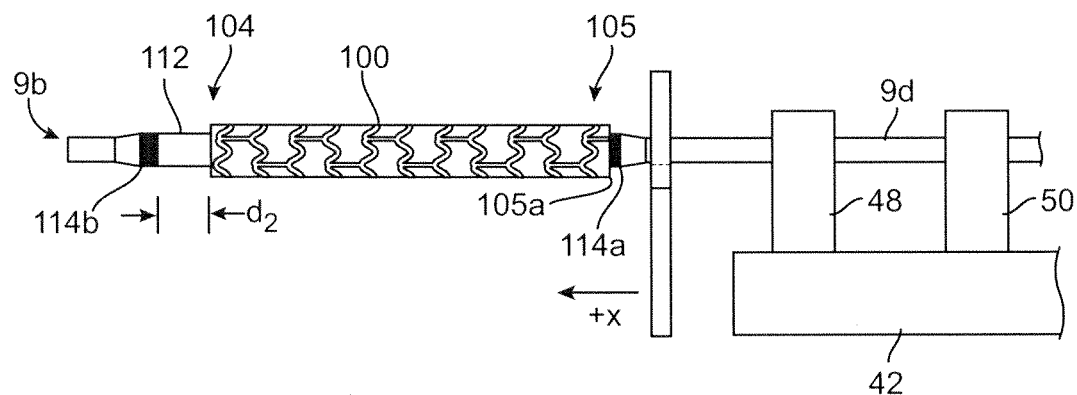
FIGS. 7A and 7B depict aspects of another example of a mechanism of a computer-controlled positioning and alignment system. In this example, a polymer scaffold is being repositioned after the scaffold has been pre-crimped to a smaller diameter
Figure 7B:
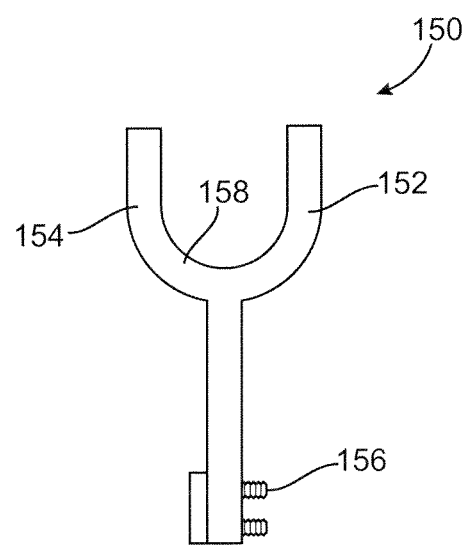

Referring to FIGS. 7A-7B there is another embodiment of a scaffold alignment mechanism. Shown is scaffold 100 after its diameter has been decreased to about ½ size of its starting diameter following a pre-crimp step, discussed in greater detail, below. A fork 150 shown in FIGS. 7A, 7B is used to engage the scaffold 100 proximal end 105b to push the scaffold 100 forward over the balloon 112 until the ends 104, 105 are between the balloon markers 114. The fork 150 is prepositioned adjacent the carriage 42, then moved forwards by a linear actuator. The fork 150 includes opposed arms 152, 154 extending upwards from a root. Connecting hardware 156 for connecting the fork 150 to an actuator arm (not shown) is shown. A inner surface 158 of the fork 150 is shaped to as a rounded surface and sized so that there is a slight clearance between the balloon surface and the surface 158. Thus, as the fork 150 moves to the left in FIG. 7A the surface 158 passes over the outer surface of balloon 112 and when reaching the scaffold 100 fork 150 abuts the end 105*a*. The fork 150 and scaffold 100 continue to move distally over the balloon 112 according to the controller logic (below) until the scaffold 100 has moved the offset distance d2 indicated in FIG. 7A.

In the case where the scaffold 100 is located too far distal, i.e., edge 104 is distal of balloon marker 114*b*, then a similar fork 150 may be disposed to the left of the scaffold to push it towards the proximal balloon marker. The same fork 150 may be used for correcting distal or proximal misalignments. The fork 150 may be re-positioned distal or proximal of the scaffold 100 depending on the alignment correction needed. When alignment is needed, it can be preferred to have misalignment always be of the type illustrated in FIG. 7A, since in these cases the catheter is brought into tension, rather than into compression, when there is scaffold-balloon interference as the scaffold 100 is moved relative to the balloon 112. As mentioned above, the scaffold 100 can be pushed towards the distal end of the balloon 112 by the fork 150 or the balloon 112 distal end can be pulled towards scaffold 100 by the carriage 42. Software code is executed by a processor and in communication with a servo mechanism controls the carriage 42 (and/or fork 150). The software code may also control the camera 60 and lighting type/source (e.g., narrow band wavelength light/white light, direct or diffused) for illumination of the marker bands 114 and/or scaffold 100. This same code may also include a routine to compute, e.g., a distance between a scaffold crown apex and balloon marker band using well known image or edge-finding computational algorithms. Thus, one or more digital images may be obtained of the scaffold and/or balloon then pixel intensities in those images examined to locate edges. A proximal edge of a marker band is found from an image taken using a first type of lighting, a distal edge of an apex of a scaffold crown is found from an image taken using a second type of lighting, then a distance is computed between these two edges to determine whether the crown apex is lying on top of the marker band. If correction is needed, the code may then command the servo mechanism to incrementally displace the scaffold or catheter relative to the other (e.g., an electric motor displaces the carriage 42 or fork 150 relative to the other by a predetermined amount, then an updated image is taken, the image analysis repeated, and updated distance computed until the distance between the balloon marker edge and crown apex is within an acceptable range of each other).

As indicated earlier, prior to a pre-crimp, a polymer scaffold diameter is can be much larger than the balloon 112 diameter (FIG. 5A). For re-alignments at this scaffold diameter, it should not make much difference whether there is a proximal or distal re-alignment needed to the left or right needed since the scaffold 100 easily moves over the balloon 112. However, when re-alignment is needed following a pre-crimp step (FIG. 7A), where the polymer scaffold diameter has been reduced to a point where it begins to engage the balloon surface, there is expected to be scaffold-balloon interaction to some degree. This follows from the purpose of the pre-crimp diameter. The diameter is chosen so that the scaffold does not easily move about, yet is still capable of being moved relative to the balloon surface when a re-alignment is needed. As alluded to earlier, this highlights another challenge faced with polymer scaffolds not present with metal stents. A large starting diameter is used for a polymer scaffold, as mentioned earlier, for mechanical performance reasons at the deployed diameter. However, the larger diameter (relative to the balloon) also increases the likelihood the scaffold will shift relative to the balloon when the initial diameter reduction is performed. There is a need, therefore, to remove the scaffold after an initial diameter reduction to verify that it is properly aligned before the scaffold is reduced to a diameter that prevents further adjustment.

When the scaffold is misaligned relative to the balloon markers as shown in FIG. 7A, the scaffold is pushed forward. Any resistance to scaffold movement by scaffold-balloon contact will produce tension in the catheter, which is acceptable. However, if the scaffold 100 is disposed distal of the distal balloon marker and needs to be re-aligned proximally, resistance to movement by balloon-scaffold contact will place the catheter distal end 9*b* into compression, which can cause the tip of the catheter to displace off axis, makes the re-alignment process more difficult (since the catheter is moving laterally while the scaffold is being repositioned).

Figure 6:
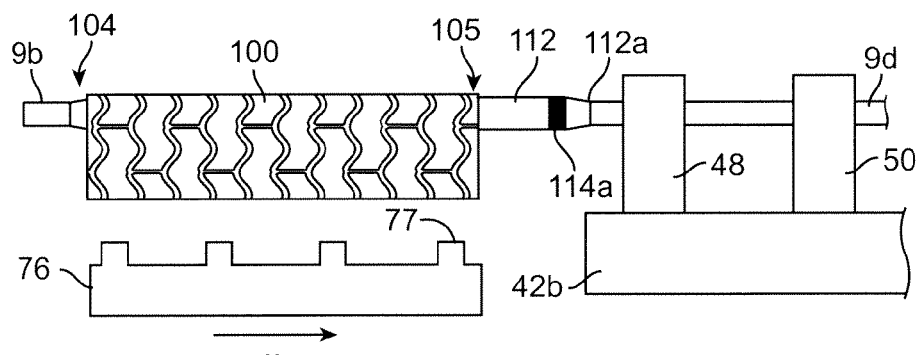
FIG. 6 is another example of a mechanism of a computer-controlled positioning and alignment system.

This problem may be addressed by holding the distal end 9*b* while the fork 150 is moved towards the proximal end, or by using an alternative mechanism (as necessary) to grip and move the scaffold while holding the distal tip on axis as the scaffold 100 is being moved. For example, in an alternative embodiment the upper surface of tray 76 from FIG. 6 is curved, or includes a pair of opposed curved surfaces that are brought together to grip the surface of the scaffold 100, then this tray is displaced to the proximally while the tip 9*d* is held on-axis. Alternatively, the initial alignment of the scaffold 100 can be proximal of the proximal balloon marker, thereby ensuring that any shifting during the pre-crimp will not result in the scaffold 100 being distal of the distal balloon marker.

The sequence of operations described above, which makes use of one or more computer-controlled actuating mechanisms, are controlled by a computer, e.g., a personal computer or PC or workstation having DRAM, disk storage, hardware bus, CPU, user input device, e.g., touch screen 16*a*, keyboard, mouse, external drives, and a network connection to a LAN and drivers for controlling the actuators used to drive the mechanisms described in FIGS. 5-6. The computer resident at station 16*a* may access information about the scaffold and catheter remotely using a LAN, WAN or other network type, which information may be accessed through a file server. The machine executable code associated with the algorithmic aspects of the positioning system may be software or hardware implemented, or a combination of both. Off the shelf equipment may be used for the imaging system 60 and actuators referred to above.

Determining a location of the scaffold edges 104, 105 and balloon distal/proximal seals 112, 114 from the camera 62 collected image(s), may be accomplished using pattern recognition algorithm, which, as mentioned earlier, can compare the camera 62 image to pre-stored information about the scaffold length and/or pattern to distinguish the scaffold 100 from the balloon 112 in the image. Distinguishing balloon markers, for example, from the scaffold and other parts of the catheter 9 may be accomplished by illuminating the scaffold and balloon with light that causes the balloon markers to illuminate light within a particular band in contrast to the surrounding image. The same technique may also be used to find the scaffold edges, based on the illumination of scaffold markers then computing the location of the scaffold edges relative to those markers. The pattern recognition algorithm may be programmed to receive as input the scaffold length, marker location and pattern, pre-crimp diameter, balloon length between proximal/distal seals and markers and output a signal to indicate the scaffold is aligned with the balloon or the offset distance, which is then received by the controller for repositioning the scaffold 100 relative to the balloon 112.

As mentioned earlier, a controller using a feedback loop may be used to reposition the scaffold on the balloon. The feedback for this controller be would position information extracted from images of intermediate positions of the scaffold relative to the balloon as the scaffold or balloon is moved relative to the other. Thus, the scaffold, for example, is moved an incremental distance and an image is taken of the new position (as described earlier). The next input to the actuator, e.g., an input to a servo, is computed based on feedback information extracted from the image, the next incremental displacement is performed, a third image is taken, etc. until the offset distance approaches zero, i.e., the scaffold is between the balloon markers. The control system may adopt a PID control, or state-space control logic for computing the next input to the actuator. The actuators may be controlled by a servo mechanism or stepper motors to provide precise control over movement of the actuators. The actuator mechanism may include a first electric motor operating a servomechanism capable of translating the scaffold and catheter to/from a semi-enclosed or shielded area (not shown). The actuators may also include a capability of rotating the scaffold and balloon once properly positioned within the camera, e.g., at 10 degree increments, to obtain images of the scaffold and/or balloon about the circumference of the scaffold-catheter assembly.

The balloon/scaffold may be separately illuminated by different light bands (e.g., X-ray light to illuminate marker bands) to obtain precise images of the balloon markers/scaffold separately from the other in addition to images taken in ambient or white light. Alternatively, or in addition, various light wavelengths may be used to preferentially illuminate the desired component in the system and block out the other (this may be preferred in the case where both the balloon polymer and scaffold polymer are transparent or semitransparent, in which case the presence of one may make it difficult to view edges of the other in white light). The light source may include filters (e.g., red blue, etc.) or the light source may utilize LEDs to generate different colored light. For example, red light can be used to make a blue catheter inner member appear black and the metallic marker bands appear white. Similarly, blue light can be used to make an orange catheter inner member appear black and the metallic maker bands appear white. The use of "color compliments" improves contrast for a scaffold-balloon visioning system. Similarly, certain wavelengths of light, light combinations, direct or diffused light can be used to generate images where relatively high intensity light is reflected from edges of the scaffold to produce clearer images of the scaffold images and also the presence of any cracks, voids or fractures in scaffold struts. Those images may then be used to find edges, orientations of struts, locate any structural integrity issues (cracking, flipping or overlapping struts, irregular crown angles among rings) using a digitized image of the scaffold crimped to the balloon.

It would, of course, be desirable to utilize a process that does not require an iterative closed or open-loop feedback control for locating a scaffold between markers. Multiple iterations, however, may be necessary when a scaffold is repositioned following pre-crimp, for the reasons alluded to earlier. When re-alignment is needed following pre-crimp the balloon may introduce enough hysteresis into the system to require an iterative approach.

As discussed earlier, pre-crimping of the scaffold seeks to provide enough friction to not cause the scaffold to easily move about, but not too much friction to prevent repositioning when needed. The pre-crimp reduces the diameter to enable more accurate measurement of the distance between the scaffold edge and the marker band. The majority of defects and scaffold movement due to distortion of the scaffold occurs during a pre-crimp step. In this sense it will be appreciated that by incorporating aspects of the disclosed alignment system following pre-crimp there is the opportunity to make fine adjustments of the scaffold when it is very close to its final diameter and shape.

Figure 8:
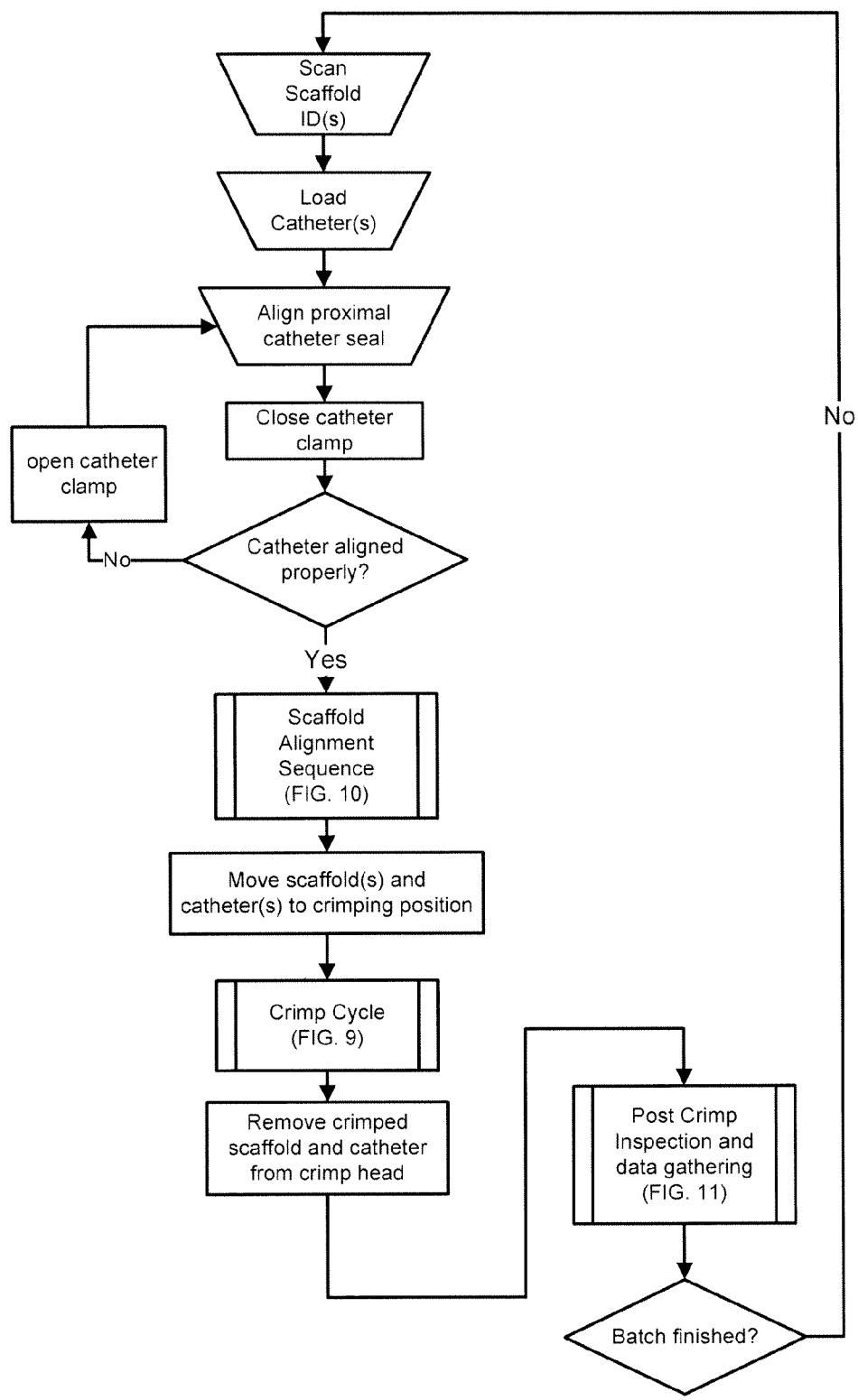
FIG. 8 is a flow process describing steps associated with the positioning and alignment of a scaffold-catheter assembly, crimping the scaffold to the catheter, and then collecting data about the scaffold crimped to the balloon using the system of FIG. 2.
Figure 9:
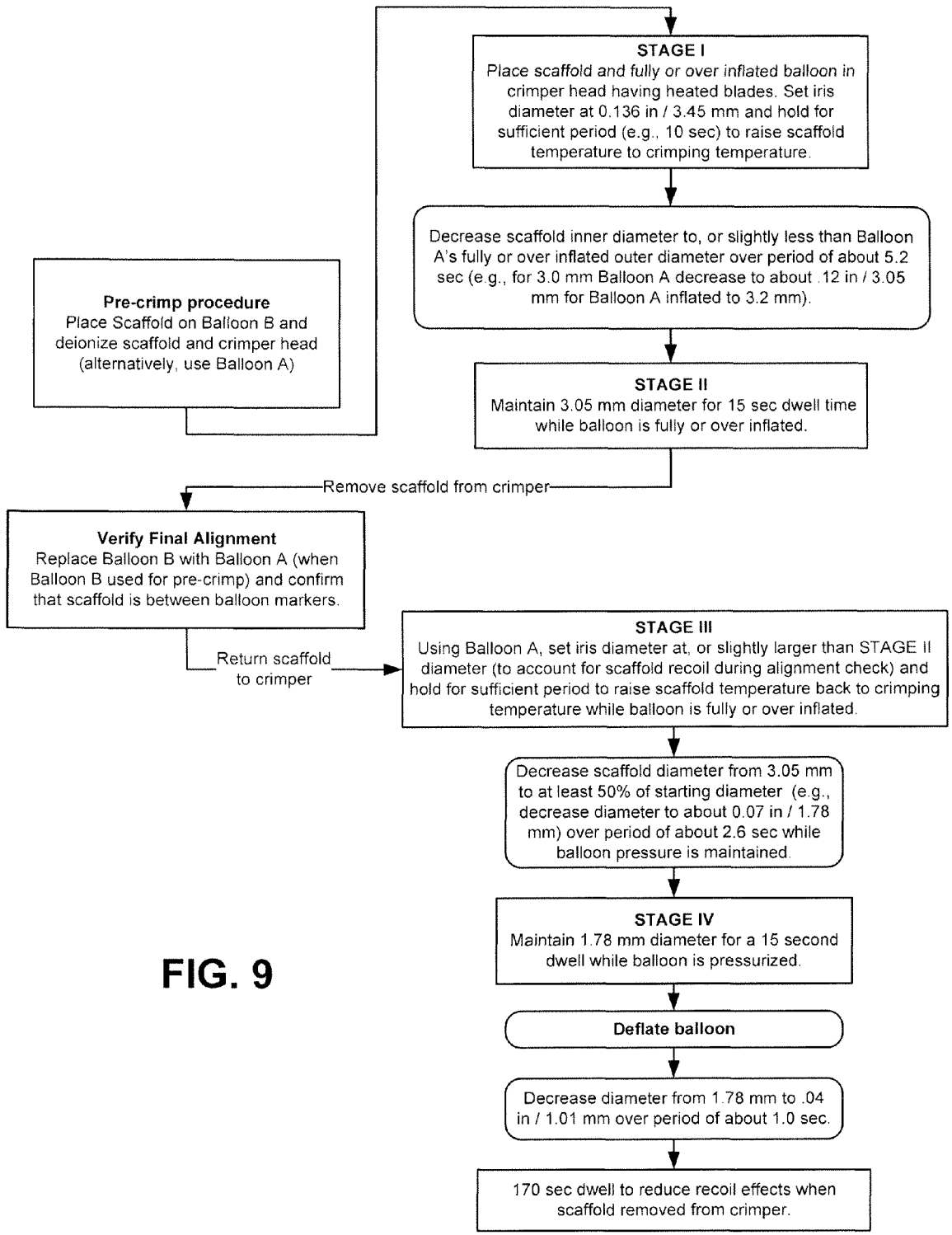
FIG. 9 is a flow process showing steps associated with crimping a polymer scaffold to a catheter balloon.
Figure 10:
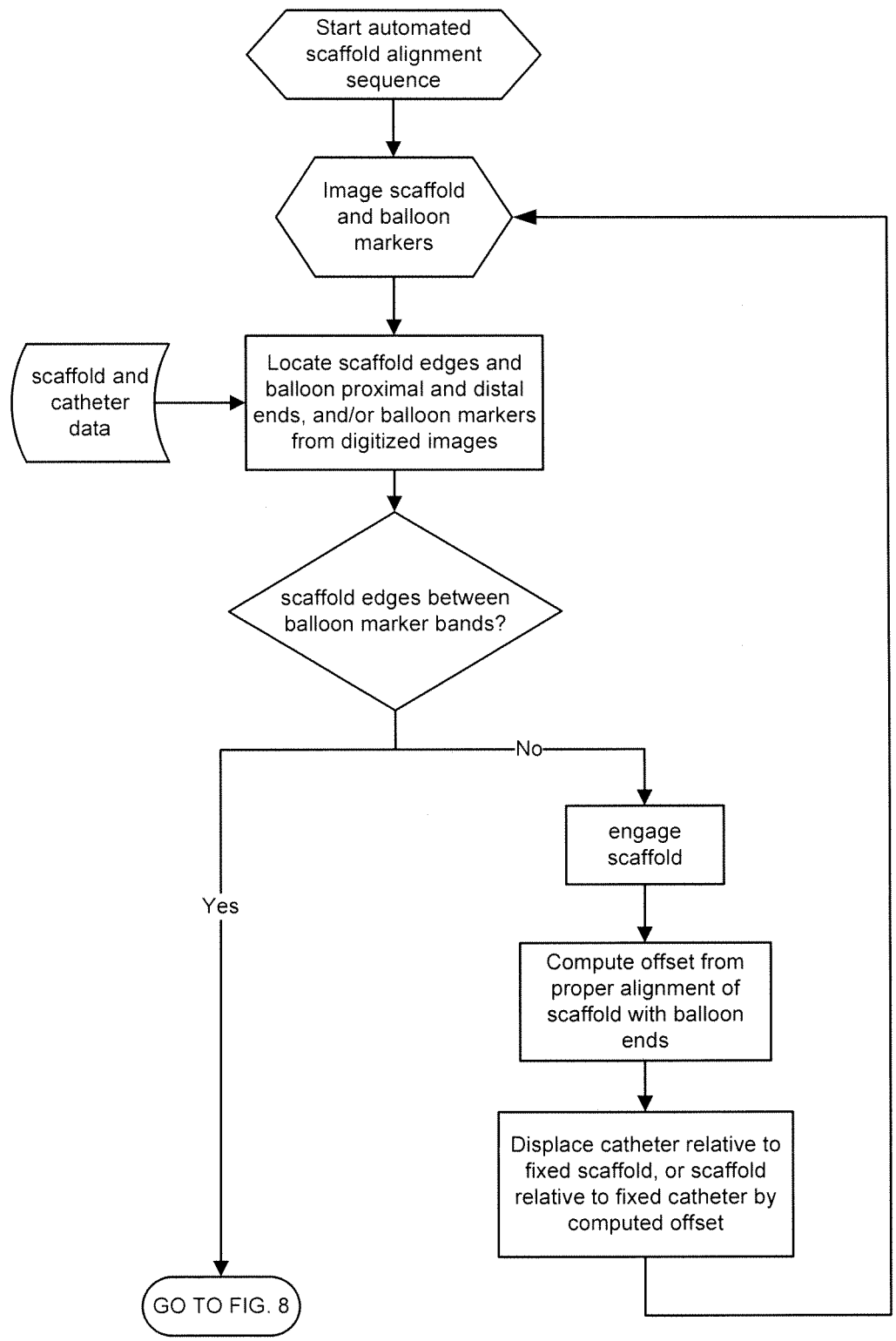
FIG. 10 is a flow process describing a process for verifying alignment of the scaffold on the balloon and repositioning the scaffold on the balloon to correct for a misalignment of the scaffold on the balloon.

FIGS. 8-10 describe process flows for positioning and aligning a catheter and scaffold and crimping the scaffold in the crimper head 20 using the system 10.

Referring to FIG. 8, the process begins by an operator reading the identification (ID) of the scaffold(s) to be crimped to a catheter. The process of positioning, aligning and then crimping is the same for a scaffold and catheter loaded at the left or right stations 14, 16 of the system 10. When both stations 14, 16 are being used to simultaneously crimp scaffolds to catheters 8, 9, a central processor may control both stations, or a separate processor at each station 14, 16 may control the process up until the point the scaffolds and catheters are ready to be inserted into the crimper head 20, at which point a central control takes over for the crimping steps. One aspect of the crimping process, a pre-crimp step, is followed by removal of the scaffold and catheter to verify alignment. For this step control may return to the station 14, 16 processor to perform a verification and possible re-alignment, followed by return of control over to a central processor (or only one station 14, 16 processor performs the crimping sequence while the other remains idle).

Referring to the process flow of FIG. 8, with the scaffold ID input to the computer control, process controls are selectable by the operator via the user display 16a, or these controls may be automatically retrieved from storage base d on the input scaffold ID. The catheter 9 is then loaded onto the alignment carriage 42. The coiled portion 9a of the catheter 9 is placed onto the tray 41. This is a manual operation performed by the operator. The catheter proximal end 9c is positioned to face the clip 9c, the coiled portion 9a is placed on the tray 41 and the shaft 9d including proximal end 9b is aligned via the rail 44 and positioned distal of the grippers 48. A luer extension is attached and the pressure source connected to the luer extension. The operator depresses a button to bring gripper pairs 50 together, thereby clamping the catheter in the carriage 42. The position of the balloon 112 proximal seal 112a relative to the distal grippers 48 is then verified by inspecting whether an illuminating light shines on the balloon proximal seal location (or a camera verifies a proper location and indicates this position by a green light, or red light if misaligned). If properly aligned, the flow next proceeds to the scaffold alignment sequence (FIG. 10), if not, the clamp is released and the operator re-positions the catheter distal end 9b until the aft balloon seal aligns with the reference light. The scaffold may be placed on the catheter manually or by an automated mounting process, as explained earlier.

Referring to the process flow of FIG. 10, with a signal received from the operator, e.g., a start button depressed, to begin the crimping sequence, control then shifts to the scaffold alignment phase (or scaffold placement on balloon and alignment phase using the same mechanism and control system) for determining whether the scaffold is properly aligned relative to the balloon markers. The positioning carriage 42 advances the catheter distal end 9b and scaffold 100 to the appropriate position for checking the alignment, i.e., the scaffold and balloon being centrally positioned at the camera 62 bore site. In this position, images collected by the camera may be used to extract distance information, relative positions of the scaffold and balloon and making adjustments to the scaffold position as described earlier.

After collecting one or more digital images, scaffold and catheter information is recalled to assist with determining the exact location of the scaffold edges and balloon markers and/or seals. For example, the distance from the distal balloon seal and balloon marker may be used to determine where the distal balloon marker is located relative to the distal seal, as in the case of the scaffold edge overhanging the balloon marker, thereby obscuring the camera 60 view of it (FIG. 5A). With information about the length of the scaffold, its pre-crimp diameter, scaffold pattern, location of its markers relative to edges, etc. the identification of the markers in the digital image, or other patterns matched to the information from the image the algorithm may determine where the scaffold edge is located.

With the scaffold edges and balloon markers located, the controller (with or without a feedback loop) determines whether the scaffold is aligned, or whether the scaffold or balloon needs to be moved relative to the other so that the scaffold is between the balloon markers (as desired) prior to crimping. If the scaffold is aligned between the balloon markers, then a control signal is passed to the central control to have the scaffold and balloon moved into the crimper head 20. If it is determined that the scaffold is not aligned, then the scaffold is moved relative to the balloon (or balloon relative to the scaffold) using, for example, the mechanisms described in FIGS. 5-7. After the scaffold has been aligned with the balloon markers, the scaffold and catheter are now ready for crimping.

There are two possible scaffold positioning sequences that would occur during the crimping process. The first would include the pre-positioning of the non-crimped scaffold on the catheter relative to the marker bands. It may be preferred during the initial alignment phase to instead bias the scaffold proximal to the desired location, such that the final positioning after pre-crimp would always be done by pushing the scaffold distal relative to the catheter and thus putting the catheter into tension, rather than compression. The second possible positioning sequence would include the re-positioning of the scaffold on the catheter after pre-crimping, before final crimp. This needs to be the final location as the scaffold cannot be moved relative to the balloon after final crimping.

Referring to embodiments of a process flow for crimping, FIG. 9, the carriage is advanced forward into the crimper head 20 under computer control to ensure the scaffold does not shift when being placed within the crimper. As indicated above, scaffold struts have not been pressed into the balloon material, but have begun to engage this material. After the pre-crimp, the scaffold and balloon are removed from the crimper head 20 so that the scaffold 100 position relative to balloon markers may be verified once again before the final crimp begins. Control then switches over to the process described in connection with FIG. 10. After that process again signals that the scaffold is aligned properly with the balloon, the scaffold and balloon are again placed within the crimper head 20. The final crimping steps begin. Examples of these crimping steps for a preferred embodiment, a PLLA scaffold crimped at a temperature near its glass transition temperature and reduced to a diameter of about 2.5 times that of the pre-crimp diameter, are shown in FIG. 9.

One or two forms of heating may be employed during the crimping process. Heating may be accomplished by heating the jaws of the crimper head, or heated air may be used in addition to heating the crimper jaws. There may be a benefit to using both heated air and convection and radiation from the crimper jaws. This combination of heat sources can cause the balloon material to flow more easily into the gaps between scaffold struts. Additionally, the use of hot air concurrently with heated jaws will reduce the temperature needed to heat the scaffold and balloon through convection and radiation from the jaws. This can be desirable so that the surface of the scaffold does not overheat and cause damage while being crimped. Thus, by using air in combination with heated jaws the jaw temperature can be lowered.

As can be appreciated from FIG. 9, there are several intermediate crimping steps, with significant dwell times needed for the polymer scaffold. This is because unacceptable cracks can develop if the diameter is reduced at too high a rate. A slow, incremental crimping process is needed so that internal stresses can work themselves out. Ideally, from a strength/integrity point of view a polymer material should be plastically deformed at an extremely slow rate (e.g., over several hours). However, this is not practical from a production viewpoint. The crimping steps illustrated in FIG. 9 were found to produce acceptable yields. When considering the significant time needed to perform a crimping sequence for a polymer scaffold as shown in FIG. 9, the advantages of an automated system 10 are appreciated.

The final crimp step, FIG. 9, can include a dwell time of 200 seconds. While the crimper jaws remain fixed in this position on the scaffold struts (for stress relaxation and minimizing recoil after the jaws are removed from the scaffold) the balloon is inflated to a pressure of about 200 psi to perform a leak test. After the leak test and 200 second dwell, the scaffold and catheter are removed from the crimper, a sheath is placed over the scaffold, and the scaffold and catheter are placed in a refrigeration unit. It has been found that there are benefits, in addition to the reduction in the time needed in the production process, to performing the leak test while the polymer scaffold is in the crimper head and restrained by the crimper jaws during the dwell time. First, by increasing the balloon pressure while at an elevated temperature, the balloon-scaffold contact can be increased as the increased pressure causes balloon folds to find their way between scaffold struts. This can increase the retention force of the scaffold on the balloon. Second, a lower scaffold-balloon profile is possible.

Figure 1A:
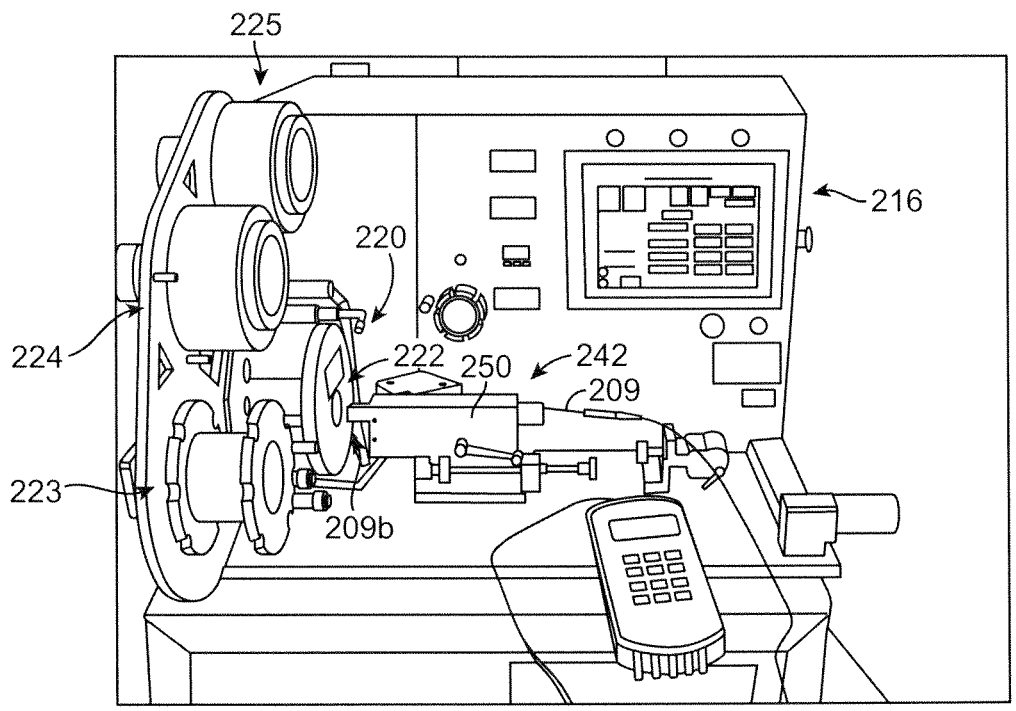
FIG. 1A is a perspective view of a crimping system according to the prior art.
Figure 1B:
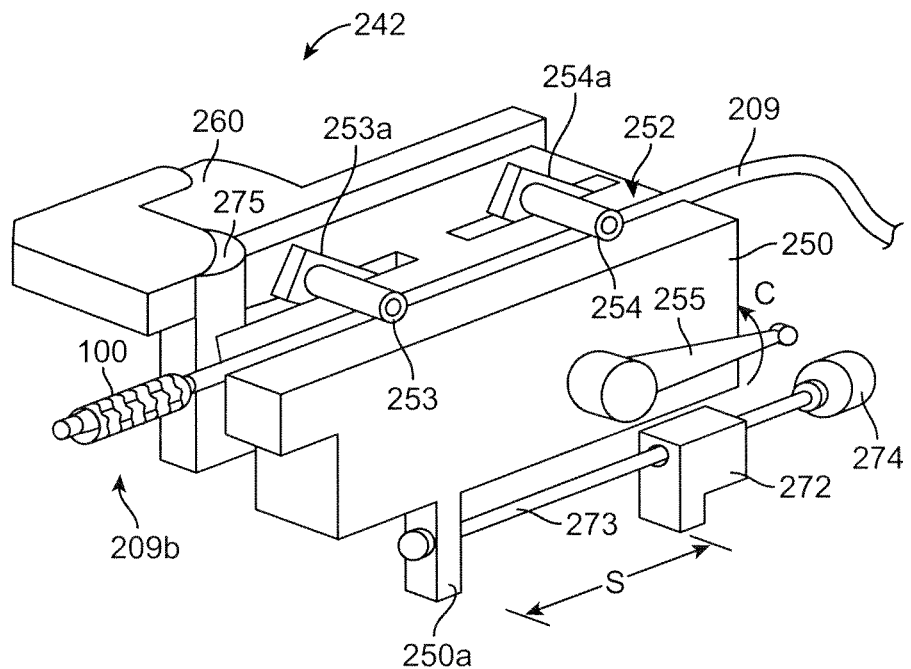
FIG. 1B is a perspective view of a carriage of the system of FIG. 1A.

In the typical case, such as when using the apparatus of FIGS. 1A-1B, the leak test is performed after the scaffold has been removed from the crimper head and inserted within the restraining sheath. The restraining sheath, being far more radially compliant than the crimper jaws, will expand to some degree when the leak test is performed. It is preferred to maintain the smallest profile as possible. Thus, if the leak test is performed in the crimper head, the smaller profile is maintained since the crimper jaws will maintain the diameter despite the increase in balloon pressure.

As discussed earlier, the restraining sheath is preferably placed over the scaffold shortly after the final crimp and the scaffold is removed from the crimper. If a restraining sheath is not placed over the scaffold in sufficient time, as explained in greater detail in U.S. application Ser. No. 13/708,638, then the scaffold will recoil, resulting in a loss of balloon-scaffold retention and increase in the crossing profile of the balloon catheter, Heretofore non-destructive testing or inspection of crimped scaffolds immediately following crimping would be done while the restraining sheath is disposed over the scaffold, which is not preferred for at least two reasons. First, a sheath disposed over the scaffold and balloon makes a visual inspection and/or measurements more difficult and unreliable, even when a relatively transparent material is used for the sheath. Second, in the typical case where a restraining sheath is manually placed over a scaffold, the manipulation of the scaffold and balloon by an operator may inadvertently affect performance of the scaffold behavior later, e.g., balloon bunching or loss of retention during the course of sliding a sheath over the scaffold. Accordingly, in the interest of monitoring the adequacy/effectiveness of crimping process parameters (e.g., heat, dwell time, final crimp position for crimper jaws, etc.) influencing the scaffold-balloon retention or uniformity of deployment from the balloon, any inspection after the sheath has been manually placed cannot account for changes induced, not by the crimping process, but by the technician when placing the sheath over the scaffold.

Figure 11:
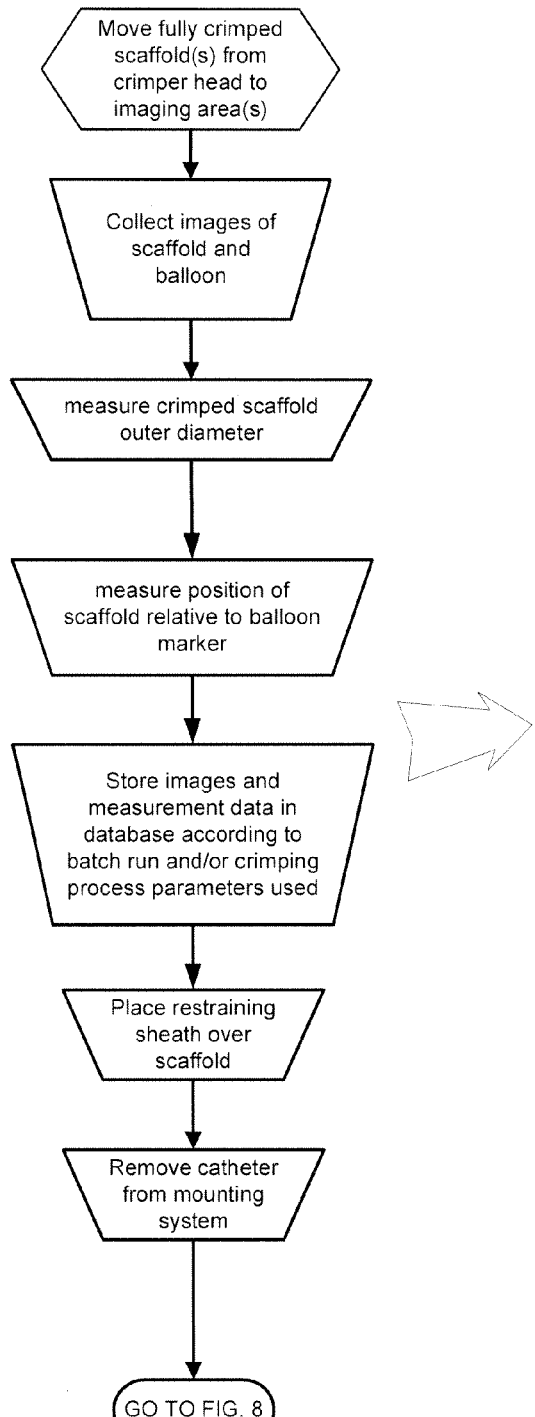
FIG. 11 is a first flow chart showing post-crimping inspection and data gathering steps when a fully crimped scaffold is removed from the crimping head and prior to placing a restraining sheath over the scaffold.
Figure 11:
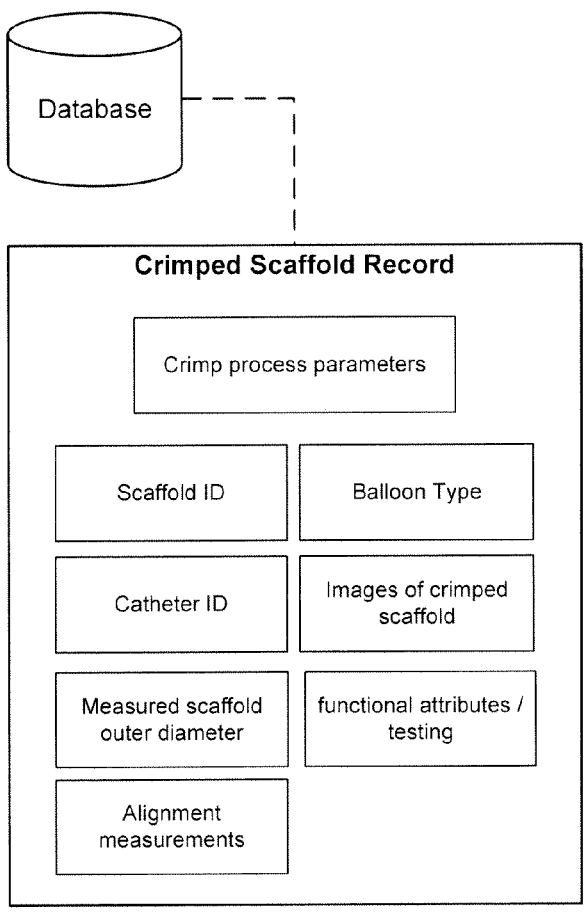

FIG. 11 shows one embodiment of a process flow for collecting data relating to a scaffold crimping process and a database schematic for storing information related to the scaffold and catheter in relation to the crimping process. Preferably this flow begins immediately after the scaffold is removed from the crimper head and prior to placing a restraining sheath over the scaffold. In the embodiment of FIG. 11 images of the scaffold are made using the visual inspection system. The scaffold is removed from the crimp head by the actuator and moved to the imaging or visual inspection system using the camera, as discussed above. During this step (or while the restraining sheath is placed over the scaffold or while the next scaffold and catheter in the batch are loaded) the positioning of the scaffold between the marker bands is checked using the camera and servo-mechanism as described earlier. The measurements taken in this step may include locating and counting any crown apex at proximal and distal ends that are not co-located with respective proximal and distal marker bands, i.e., whether any crown apex is not disposed over a marker band. The outer diameter of the scaffold may be measured as well, either at the time of image collection or shortly afterwards using the images. The outer diameter measurements may include measuring the largest diameter over the length, the diameters at ends, middle, or at each ring.

The inspection process may also include the gathering of images of the scaffold and balloon and scaffold separately from the balloon utilize the combinations of lighting as discussed earlier. Thus, a plurality of image over the crimped scaffold body are collected, e.g., for every 90 degrees or 45 degrees rotation about the scaffold longitudinal axis, for purposes of inspecting the structural integrity of the scaffold, e.g., non-uniform crown angles, cracking or fracture of struts, overlapping struts, flipping of struts, etc. processor software causes the actuator to translate and rotate the scaffold as needed into position for image collection, measuring the outer diameter and position between balloon markers. The collected images may be stored in a database containing records as indicated in FIG. 11. As also indicated in the "Crimped Scaffold Record" there may also be linked to the database information concerning testing or evaluation of functional attributes, including destructive testing performed on samples from each batch run for purposes of generating statistical information relating the crimping process to functional attributes of the tested samples. The testing information may include destructive testing such as measurements of the scaffold-balloon retention force, the deploy-to-fracture diameter, the scaffold acute recoil, and the uniformity of deployment. Non-destructive testing may include examination of the number of cracks or voids, the arrangement of balloon folds over the length of the scaffold, the variance in crown angles from ring-to-ring, the outer diameter six months after crimping, etc.

Figure 12:
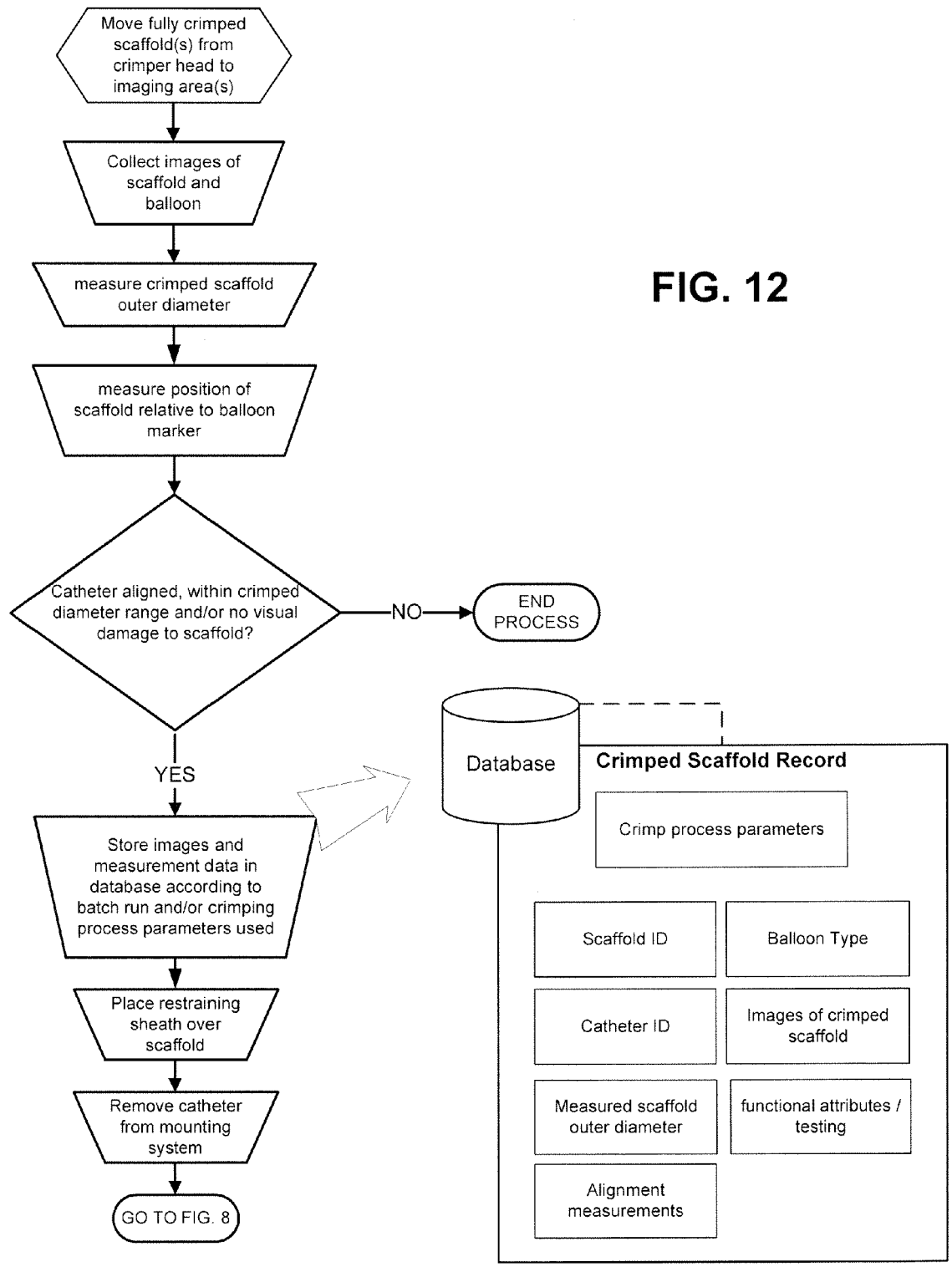
FIG. 12 is a second flow chart showing post-crimping inspection and data gathering steps when a fully crimped scaffold is removed from the crimping head and prior to placing a restraining sheath over the scaffold.

FIG. 12 shows a flow process that includes a pass/fail criterion for the crimping process. The pass/fail check of outer diameter, alignment between markers and/or visual damage to the scaffold (e.g., cuts, gauges, fractures, overlapping struts) may be included within the software code that collects images and performs measurements. As explained above, the software may include or call a routine that performs a pixel analysis of the digitized image to identify any prominent damage caused by the crimper head. If the scaffold passes these checks then the data may be stored (or the data may be stored in the event of failure as well) and the process continues. The pass/fail criterion may also include a check against the programmed crimping process parameters and the actual implementation of those parameters during the crimping process. This measure may help to ensure there are no violations of the process conditions (e.g., pressure, force, temperature, etc.).

After collecting a sufficient number of samples of scaffolds crimped to balloons for a particular set of crimping process parameters, e.g., scaffold temperature, balloon pressure, crimp time, crimp speed, and target diameter, a later modification of a processing parameter and image collection for scaffolds crimped using the modified processing parameters can be compared to the images collected for crimped scaffolds using the prior processing parameters. From this type of data comparison statistics may be generated to predict the most likely effect of changing one or more crimp processing parameters. These statistics can be used to help decide what amount of destructive testing is needed when a production process parameter is changed, or to anticipate the most likely cause for a problem or solution to fix a problem encountered during a manufacturing process. For example, an inconsistent outer diameter of the crimped scaffold may be found in this data, which would indicate a potential problem with the crimper jaw bearings or blade alignment. If the outer diameter is measured only after the restraining sheath is removed, then it would not be known whether the inconsistency was due to operator errors or, e.g., a need to replace bearings in the crimping device.

Additionally, utilizing the information in the database there may be generated reliable statistics that can justify a relaxing of specifications for the scaffold-catheter assembly or to determine what single or combination of crimping process parameters most directly affect a particularly functional attribute. For example, it may be found that a relaxing of an alignment tolerance to permit some crown apexes to not lie on a balloon marker is justified based on there being no statistical significance between crimped scaffolds where as few as one crown apex is on a balloon marker (as opposed to all on the marker, or a majority thereof) and an unfavorable outcome during destructive testing, e.g., non-uniform deployment. Or there is found a statistical significance between a crimping temperature reduction of a few degrees and less fractures (or acute recoil) when the scaffold is deployed within a lumen. By being able to generate information through the automated process (prior to manipulation of a scaffold or prior to placing a sheath over the scaffold) a more direct link between a crimping process and functional outcome can be assessed.

Another advantage of the automated process pertains to leak testing. In some cases a leak test is done after removing the crimped scaffold from the crimper and placing a sheath over the scaffold. The scaffold balloon then is connected to a leak tester pressure source and the balloon pressurized within the sheath to check for any leaks. The automated process enables leak testing in the crimp head then automated collection of images and measurement taken after the leak test is performed, without disturbance/damage from a manual sheath fitting process.

In other embodiments the crimping system may include a database of scaffold and balloon data, and failure/acceptance criteria for determining based on the images collected before placing the restraining sheath whether the crimped scaffold is acceptable, unacceptable or requires manual inspection as described in the processes set forth in U.S. Pat. No. 8,311,312 and in particular the attributes of the database 30, and process of FIG. 18. This disclosure is directed to a stent inspection system based on collecting images of a stent. However, in an alternative embodiment it will be appreciated that the same logic steps of accepting or rejecting the medical device, statistics and related numerical-based criteria described in U.S. Pat. No. 8,311,312 are within the scope of the scaffold-inspection embodiments of the invention using the post-crimping images with or without the pre-crimping images.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the scope of this invention.

What is claimed is:

1. A method for crimping a scaffold to a balloon of a balloon catheter, comprising:
   inserting the balloon and scaffold into a crimper head using an actuator including a carriage;
   performing a first crimping of the scaffold to the balloon to produce a pre-crimped scaffold;
   removing the pre-crimped scaffold from the crimper head, and
   collecting an image of the scaffold and the balloon to determine whether there is a misalignment between the pre-crimped scaffold and the balloon, whereupon detection of a misalignment a servo mechanism displaces one of the pre-crimped scaffold and the balloon relative to the other while a fork, cradle or arm is engaged with struts of the scaffold;
   returning the scaffold and balloon to the crimper head; and
   performing a second crimping of the scaffold to the balloon to produce a final crimped scaffold.

2. A method of crimping a scaffold to a balloon of a balloon catheter, comprising:
   aligning the scaffold with the balloon, including
      placing the scaffold on the balloon,
      collecting at least one first image of the scaffold on the balloon, and
      using the at least one first image and a servo mechanism, displacing one of the scaffold and the balloon relative to the other while a fork, cradle or arm is engaged with struts of the scaffold until the scaffold is aligned with the balloon; and
   crimping the scaffold to the balloon including placing the scaffold in a crimper head.

3. The method of claim 2, further including
   collecting at least one second image of the crimped scaffold; and
   after collecting the at least one second image, placing the crimped scaffold into a sheath.

4. The method of claim 3, further including the step of placing the sheath over the scaffold within two minutes of removing the scaffold from the crimper head.

5. The method of claim 4, further including using the at least one second image to measure an outer diameter of the crimped scaffold before placing the sheath over the crimped scaffold.

6. The method of claim 4, further including using the at least one second image to measure a distance between a scaffold crown and a balloon marker, or the number of crowns disposed over a balloon marker.

7. The method of claim 2, wherein the scaffold is supported by a carriage and the aligning step further includes
   positioning the arm between struts of the scaffold,
   moving one of the arm and the carriage while the other is held stationary, and
   when the scaffold is aligned with the balloon the arm is withdrawn from the scaffold.

8. The method of claim 2, wherein the aligning step further includes collecting at least one second image after the displacing one of the scaffold and the balloon relative to the other, and then displacing, for a second time, one of the scaffold and the balloon relative to the other.

9. The method of claim 2, wherein the balloon is supported upon a carriage and the balloon is displaced while the scaffold is held stationary during the aligning step, further including the step of placing the aligned scaffold and balloon into the crimp head by displacing the carriage towards the crimp head using an actuator connected to the carriage.

10. The method of claim 2, wherein the placing the scaffold on the balloon includes the step of placing the scaffold on the cradle and, using an actuator, inserting the balloon into a bore of the scaffold while the scaffold is supported by the cradle.

11. The method of claim 2, wherein the scaffold is supported by a carriage and the aligning step further includes
   positioning the fork at an end of the scaffold,
   engaging the scaffold with the fork by moving one of the fork and the carriage while the other is held stationary, and
   when the scaffold is aligned with the balloon the fork is withdrawn from the scaffold.

12. The method of claim 11, wherein the fork has opposed arms extending upwardly from a root.

13. The method of claim 11, wherein the fork has a rounded inner surface, such that when the scaffold is engaged by the fork, the inner surface is clear of a balloon surface while the inner surface is engaged with the scaffold, thereby permitting relative movement between the scaffold and balloon.

14. A method for crimping a scaffold to a balloon of a balloon catheter, comprising:
   inserting the balloon and scaffold into a crimper head;
   crimping the scaffold to the balloon to produce a crimped scaffold;
   removing the crimped scaffold from the crimper head;
   placing a restraining sheath over the crimped scaffold; and
   collecting images of the crimped scaffold and balloon, comprising collecting a first image using a first light to locate a balloon marker, and collecting a second image using a second light to locate an edge of the scaffold, wherein the second light is different from the first light.

15. The method of claim 14, wherein the collecting images step takes place at least during one of before the scaffold and balloon are inserted into the crimper head, and after the crimped scaffold is removed from the crimper head and before the restraining sheath is placed over the crimped scaffold.

16. The method of claim 14, wherein the first image collected using the first light illuminates scaffold edges and the second image collected using the second light illuminates balloon markers.

17. The method of claim 14, wherein the first light is X-ray light, blue light or red light.

18. The method of claim 14, wherein the first and second lights are color complements and the first and second lights are generated from light emitting diodes (LEDs) or a white light source and filter, selected to contrast balloon markers from edges of the scaffold.

19. The method of claim 14, wherein the second light is a direct light that reflects from edges of the scaffold to identify edges, orientations of struts, irregular crown angles, and/or to identify cracks, voids or fractures in scaffold struts.

20. The method of claim 14, wherein the collecting images step further includes collecting images for every 90 or 45 degrees of rotation about a scaffold longitudinal axis.

* * * * *